(12) United States Patent
Saladino

(10) Patent No.: US 10,722,403 B2
(45) Date of Patent: Jul. 28, 2020

(54) HEADWEAR WITH STORABLE ACCESSORY

(71) Applicant: GOOD.B, LLC, Cardiff, CA (US)

(72) Inventor: Gregory Saladino, Cardiff, CA (US)

(73) Assignee: GOOD.B, LLC, Cardiff-by-the-Sea, CA (US)

( * ) Notice: Subject to any disclaimer, the term of this patent is extended or adjusted under 35 U.S.C. 154(b) by 404 days.

(21) Appl. No.: 15/481,316

(22) Filed: Apr. 6, 2017

(65) Prior Publication Data

US 2017/0216099 A1     Aug. 3, 2017

Related U.S. Application Data

(63) Continuation-in-part of application No. 14/831,719, filed on Aug. 20, 2015, now abandoned, which is a
(Continued)

(51) Int. Cl.
| | |
|---|---|
| *A42C 5/00* | (2006.01) |
| *A61F 9/02* | (2006.01) |
| *A42B 1/24* | (2006.01) |
| *A42B 3/18* | (2006.01) |
| *A41D 13/11* | (2006.01) |

(Continued)

(52) U.S. Cl.
CPC .............. *A61F 9/029* (2013.01); *A41D 3/005* (2013.01); *A41D 13/1153* (2013.01); *A42B 1/048* (2013.01); *A42B 1/241* (2013.01); *A42B 1/247* (2013.01); *A42B 3/185* (2013.01); *A41D 2200/20* (2013.01)

(58) Field of Classification Search
CPC .. A41D 15/002; A41D 15/005; A41D 15/007; A41D 15/004; A41D 2200/20; A42B 1/206; A41F 19/005; A41F 19/00
See application file for complete search history.

(56) References Cited

U.S. PATENT DOCUMENTS

| | | | |
|---|---|---|---|
| 2,615,168 A | 10/1952 | Tannenbaum | |
| 2,839,757 A * | 6/1958 | Gianola | A42B 1/045 2/205 |

(Continued)

FOREIGN PATENT DOCUMENTS

KR     20-0239252 Y1     10/2001

OTHER PUBLICATIONS

Frostline Hat™ Style #82045OR. Website: http://www.outdoorresearch.com/en/frostline-hat.html. Web. (2010) 3 pages. [Retrieved Oct. 2, 2014].

(Continued)

*Primary Examiner* — Timothy K Trieu
(74) *Attorney, Agent, or Firm* — Mintz Levin Cohn Ferris Glovsky and Popeo, P.C.

(57) ABSTRACT

Headwear includes a storage region formed in a headwear portion with the storage region having an opening. An accessory is configured to cover a portion of a wearer's face and includes first and second opposing ends. The first end of the accessory is manually removable from the storage region through the opening. A retainer is attached to the second end of the accessory for limiting movement of the accessory within the storage region. The retainer locks the second end of the accessory within the storage region.

16 Claims, 32 Drawing Sheets

Related U.S. Application Data continuation-in-part of application No. 14/452,380, filed on Aug. 5, 2014, now Pat. No. 10,226,086, which is a continuation-in-part of application No. 13/507,389, filed on Jun. 25, 2012, now Pat. No. 9,364,040.

(60) Provisional application No. 61/862,145, filed on Aug. 5, 2013, provisional application No. 62/319,228, filed on Apr. 6, 2016, provisional application No. 62/348,073, filed on Jun. 9, 2016.

(51) Int. Cl.
*A41D 3/00* (2006.01)
*A42B 1/04* (2006.01)

(56) References Cited

U.S. PATENT DOCUMENTS

| | | | |
|---|---|---|---|
| 3,750,192 A | 8/1973 | Beresic | |
| 3,765,031 A | 10/1973 | Beresic | |
| 4,302,850 A | 12/1981 | Maeshima | |
| RE30,899 E * | 4/1982 | Kallman | A41D 27/00 2/94 |
| 4,689,831 A | 9/1987 | Greenberger et al. | |
| 4,773,101 A | 9/1988 | Kapp et al. | |
| 5,062,163 A * | 11/1991 | Avey | A42B 1/067 2/410 |
| 5,105,475 A | 4/1992 | Lynd et al. | |
| 5,369,809 A | 12/1994 | Hall | |
| 5,473,778 A * | 12/1995 | Bell | A42B 1/247 2/10 |
| 5,539,929 A | 7/1996 | Revson | |
| 5,713,077 A | 2/1998 | Humbrecht | |
| 5,794,276 A * | 8/1998 | Walker | A41D 13/11 128/202.19 |
| 5,815,832 A | 10/1998 | Skolik | |
| 5,860,165 A | 1/1999 | Cvijanovich | |
| 5,894,604 A | 4/1999 | Crabb et al. | |
| 5,926,854 A | 7/1999 | Grilliot et al. | |
| 5,933,871 A | 8/1999 | Kraft | |
| 6,170,087 B1 | 1/2001 | Brannon | |
| 7,240,372 B2 * | 7/2007 | Larson | A41D 13/11 2/173 |
| 7,260,850 B2 | 8/2007 | Ambuske et al. | |
| 7,690,052 B2 | 4/2010 | Saladino | |
| 8,001,624 B1 | 8/2011 | Leedom | |
| 9,364,040 B2 | 6/2016 | Saladino | |
| 9,512,873 B2 | 12/2016 | Oguma et al. | |
| 9,521,873 B1 * | 12/2016 | Mignone | A41D 13/1161 |
| 2002/0100106 A1 * | 8/2002 | Simmons | A42B 1/008 2/171.2 |
| 2006/0117450 A1 | 6/2006 | Matsumoto | |
| 2008/0250538 A1 | 10/2008 | Saladino | |
| 2009/0019616 A1 | 1/2009 | Smith et al. | |
| 2009/0210995 A1 | 8/2009 | Kwon et al. | |
| 2011/0185482 A1 | 8/2011 | Godfrey et al. | |
| 2011/0252547 A1 | 10/2011 | Leung et al. | |
| 2012/0060259 A1 | 3/2012 | Falken | |
| 2013/0340142 A1 | 12/2013 | Saladino | |
| 2014/0345029 A1 | 11/2014 | Saladino | |
| 2015/0223527 A1 * | 8/2015 | Arora | A41D 13/0125 2/86 |
| 2016/0015099 A1 | 1/2016 | Saladino | |

OTHER PUBLICATIONS

International Search Report issued in International Application No. PCT/US2013/047160, dated Oct. 4, 2013.

\* cited by examiner

HEADWEAR WITH STORABLE ACCESSORY

CROSS-REFERENCE TO RELATED APPLICATIONS

This application is a continuation-in-part of U.S. patent application Ser. No. 14/831,719, titled "Apparel With Retractable Extensions," filed Aug. 20, 2015, which is a continuation-in-part of U.S. patent application Ser. No. 14/452,380, titled "Apparel With Retractable Extensions," filed Aug. 5, 2014, claims priority to U.S. Provisional Patent Application Ser. No. 61/862,145 filed Aug. 5, 2013 and is a continuation-in-part of U.S. patent application Ser. No. 13/507,389, titled "Apparel With Retractable Extensions," filed Jun. 25, 2012 and issued as U.S. Pat. No. 9,364,040. This application also claims priority to U.S. Provisional Patent Application Ser. No. 62/319,228, titled "Headwear With Storable Accessory," filed Apr. 6, 2016 and to U.S. Provisional Patent Application Ser. No. 62/348,073, titled "Headwear With Storable Accessory," filed Jun. 9, 2016. The disclosures of the aforementioned applications are hereby incorporated by reference, each in its entirety.

TECHNICAL FIELD

The subject matter described herein relates to headwear, and more particularly to an article of headwear such as a cap, hat, headband, headset, disposable medical head covers, hood or helmet, helmet covering and an accessory, such as a goggle, a virtual reality headset, a mixed reality headset, a holographic lens, 3D glasses, a camera, a video camera, a sun shade, Google Glasses, an optimal head-mounted display, a cell phone, a smart phone, a cell phone encasement, a medical mask, a protective medical eye shield, a disposable medical face covering or bandanna, stored in the headwear and selectively moved into a position over the wearer's face.

BACKGROUND

During the performance of many activities, such as skiing and riding a motorcycle, an individual wears an item of headgear, such as a ski hat or helmet, while also using an accessory, such as a pair of ski goggles or a bandanna to protect his face while he is engaged in the activity.

U.S. Pat. No. 7,690,052, describes how a goggle band may be securely retained to the upper or forehead portion of a ski hat in order to prevent the goggle from being separated from the hat. The goggle can be pivoted downward to cover the wearer's eyes and face, when desired, and be raised back to its original position at the conclusion of the activity (e.g. skiing). Other hat constructions that include a face-covering accessory are disclosed in U.S. Pat. No. 7,260,850 to Ambuske et al; U.S. Pat. No. 5,815,832 to Skolik; US Pub. 2011/0185482 to Godfrey; Pub. No. 2006/0117450 to Matsumoto; and U.S. Pat. No. 5,105,475 to Lynd et al., the contents of each are hereby incorporated by reference.

SUMMARY

In one aspect, headwear includes a storage region formed in a headwear portion with the storage region having an opening. An accessory is configured to cover a portion of a wearer's face and includes first and second opposing ends. The first end of the accessory is manually removable from the storage region through the opening. A retainer is attached to the second end of the accessory for limiting movement of the accessory within the storage region. The retainer locks the second end of the accessory within the storage region.

In some variations one or more of the following features can optionally be included in any feasible combination.

The retainer can include a retention element having a dimension greater than that of the opening of the storage region. The second end of the accessory is prevented from being removed from the storage region through the opening. Also, the retainer can include a retention element having a first end attached to the second end of the accessory, and a second opening at a rear of the storage region through which the retention element passes.

The headwear can include a locking element in which the position of the locking element relative to the storage region is adjustable, allowing the selective loosening and tightening of the accessory when covering the portion of the wearer's face.

The headwear can also include a retracting element for manually returning the accessory to the storage region.

The headwear portion can include a layer that is non-permeable to moisture positioned adjacent the storage region for preventing the passage of moisture from a wearer's head through the headwear portion to the accessory when the accessory is stored in the storage region.

The headwear portion can also have a first side and a second side, the second side opposing the first side, and the storage region formed in the first side. A detachable element can detachably secure the first end of the accessory at a location at the second side of the headwear portion after the first end of the accessory has been removed from the storage region and pulled to a second position over the wearer's face. The detachable element can include cooperating male and female hook and loop fabric tabs. The headwear portion can be an eyeglass.

The accessory can be a lens, an encasement comprising an encasement opening shaped to receive a smartphone, or a camera retractably attached to the storage region with a retractable element allowing manual extension and retraction of the camera from the storage region.

The headwear further can include an EMF blocker between the storage region and a wearer's head for preventing the passage of EMF rays.

The storage region can be removably connected to the headwear portion.

In an interrelated aspect, headwear includes a headwear portion having opposite sides. The headwear also has an accessory removably stored in a first position on one side of the headwear, the accessory being manually removable from the first position and horizontally movable to detachably secure to a second position where the accessory covers a portion of the wearer's face.

In some variations one or more of the following features can optionally be included in any feasible combination.

The accessory can be a lens that slides horizontally on a track formed in the headwear portion.

The headwear portion can include a frame comprising a horizontal track operatively connected to a locking element, the first position corresponding to the locking element being at a first end of the horizontal track and the second position corresponding to the locking element being a second end of the horizontal track.

The headwear can also include at least one of a non-permeable layer and an EMF blocker between the accessory and a head of a wearer.

In an interrelated aspect, headwear includes a headwear portion comprising a first side and a second side opposite the first side. The headwear also has an accessory removably secured by a first detachable element to the first side of the headwear portion in a first storage position, when not in use. The headwear also includes a second detachable element secured to the second side of the headwear portion, the accessory being manually detachable from the first storage position and movable across a wearer's face to a second position in which the first detachable element is detachably secured to the second detachable element, the accessory being manually detachable from the second position and returnable to the first storage position after the accessory has been detached the second position.

In some variations one or more of the following features can optionally be included in any feasible combination.

The accessory can be a lens that slides in a horizontal direction to cover the portion of the wearer's face.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 10b illustrates a top view of the embodiment of FIG. 10a;

When practical, similar reference numbers denote similar structures, features, or elements.

DESCRIPTION

Figure 1:
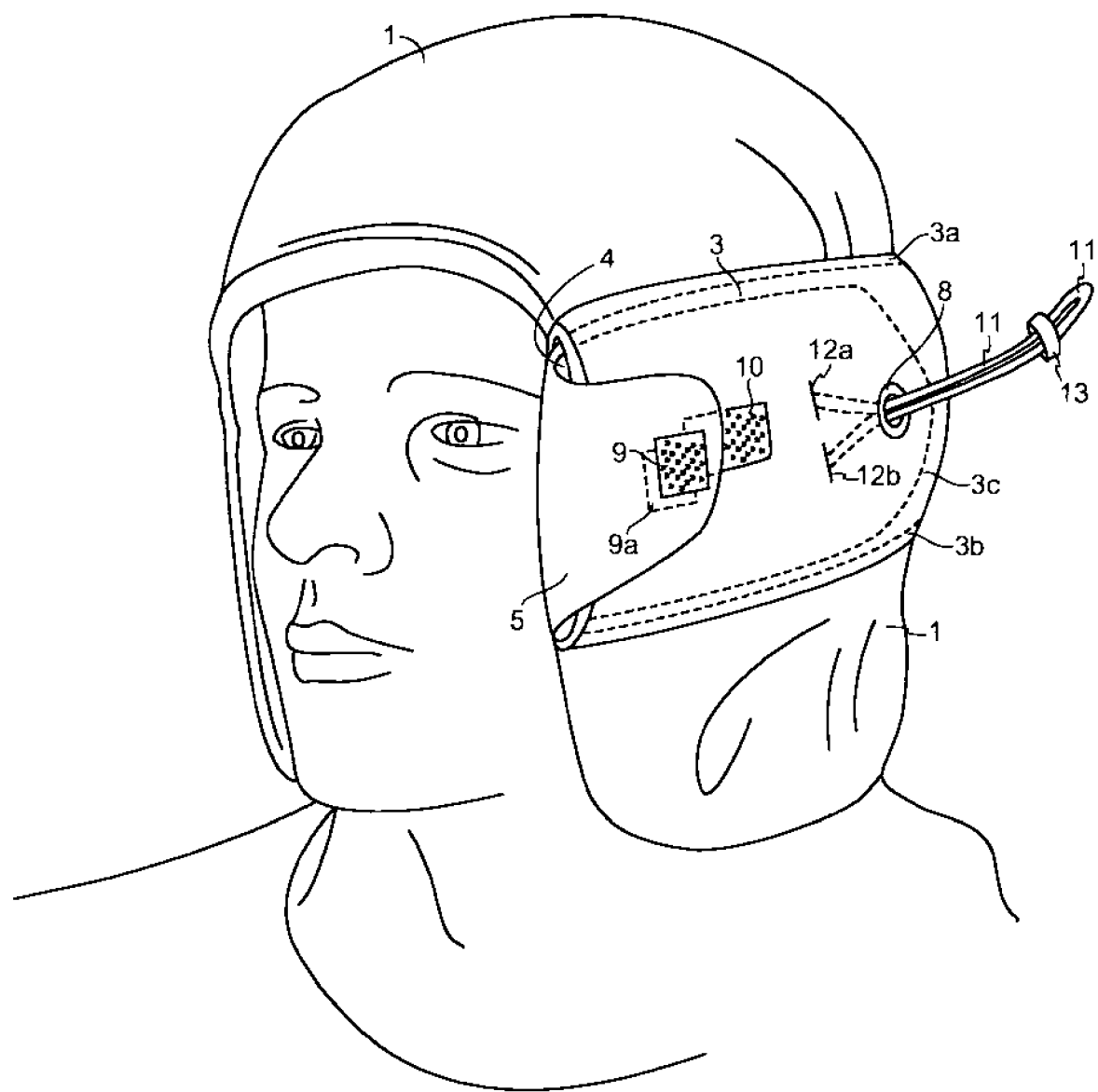
FIGS. 1-4 are side elevations illustrating a hat and goggle arrangement in accordance with a first embodiment.

The details of one or more variations of the subject matter described herein are set forth in the accompanying drawings and the description below. Other features and advantages of the subject matter described herein will be apparent from the description and drawings, and from the claims. While certain features of the currently disclosed subject matter may be described for illustrative purposes in relation to headwear with storable accessories, it should be readily understood that such features are not intended to be limiting.

Implementations of the current subject matter can include, but are not limited to, articles of manufacture (e.g. apparatuses, systems, etc.), methods of making or use, compositions of matter, or the like consistent with the descriptions provided herein.

FIGS. 1-4 are side elevations illustrating a hat and goggle arrangement in accordance with a first embodiment. There is shown in FIGS. 1-4 a first embodiment of the present invention as it used with an article of headwear or a hat 1 and a goggle band 5 (not shown in FIG. 1). A material 3 is affixed to one side of hat 1 as by upper and lower horizontal stitches 3*a* and 3*b*, which form an opening or pocket 4. The rear edge 3*c* of pocket 4 may be left open or sewn closed. Material 3 may be made of neoprene, foam, canvas, cotton, flannel, plastic, or a thermoformed plastic. A male Velcro tab 10 is placed on the outer surface of material 3 toward the front of the wearer's face. Pocket 4 may be situated in a horizontal position, or it may be angled upward toward the top of the head or downward toward the wearer's neck. The pocket may also be located toward the rear of the hat or situated on the inside of the hat, or positioned in between an internal and external lining of a dual-layered hat. Headwear 1 may also exist as a headband, a hood of a hooded sweatshirt, a military helmet, a construction helmet, a motorcycle helmet, or a snowboard helmet.

Figure 2:
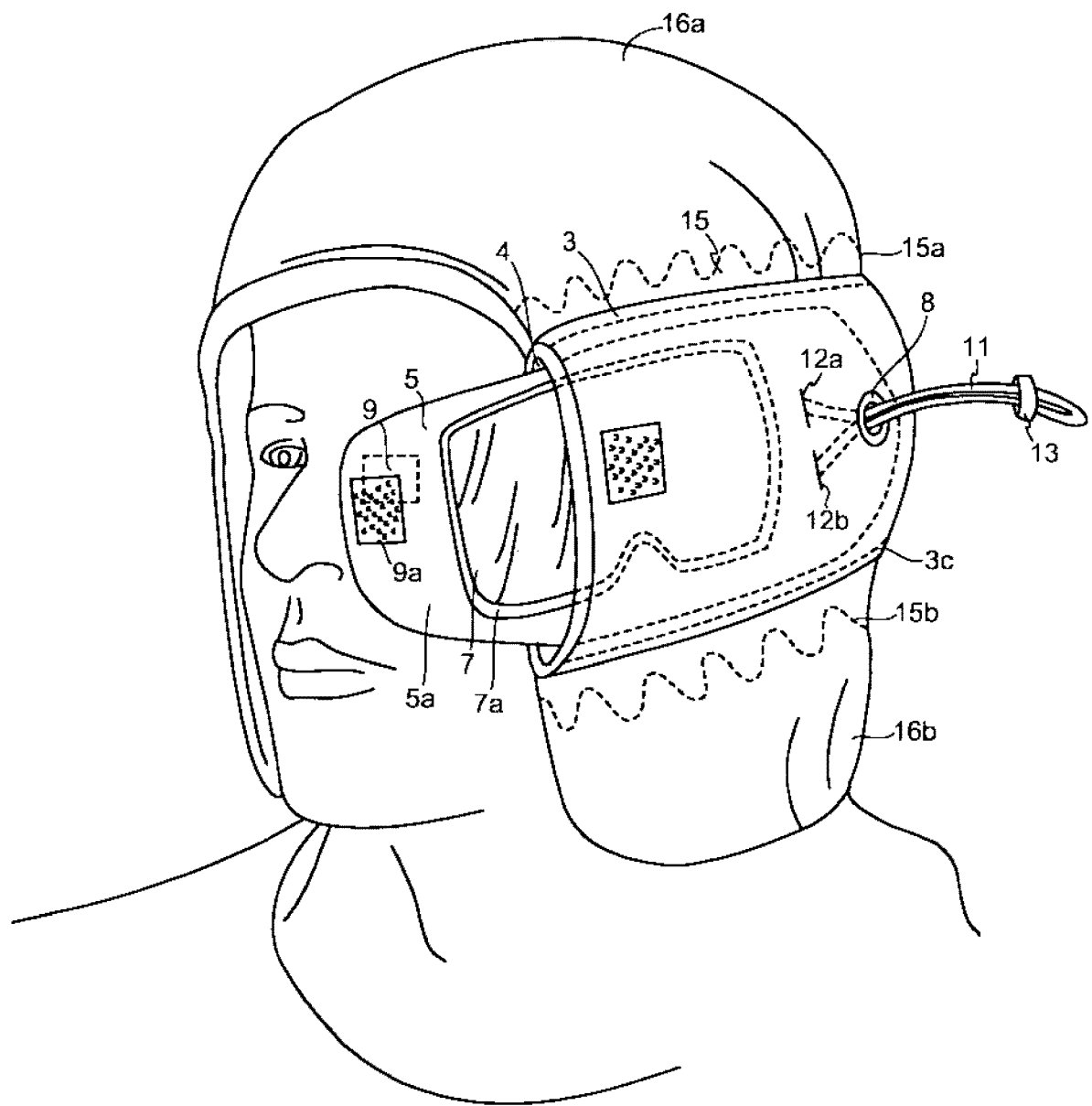

As can be seen in FIG. 2, the goggle band 5 is normally, that is, when not deployed by the wearer, stored in pocket 4. A retention string 11 is attached to the inner end of the goggle band 5 at a contact point 12*a*. String 11 extends out of pocket 4 through a grommet 8 on material 3. The string 11 then passes through a cord lock 13, makes a loop, passes back through cord lock 13, reenters pocket 4 through grommet 8, and is reattached to the inner end of goggle band 5 at contact point 12*b*.

The other, free end of the goggle band 5 protrudes out from the pocket 4 toward the front end of the hat and is folded back on itself and attached to material 3 by means of a female Velcro tab 9*a* attached to the underside of the free end of the goggle band. When the goggle band 5 is in the position shown in FIG. 2, stored within pocket 4, the exposed Velcro tab 9 is not in use. Other separably detachable elements, such as a buttons and slits, hooks and loops, latches, closure mechanisms, button snaps, snap grommets, or magnets with metal connecting tabs may be used in place of the Velcro tabs 9, 9*a*.

When the wearer wishes to cover his eyes with the goggle, such as a skier about to descend a slope, he grabs the free end of goggle band 5 with one hand, thereby separating Velcro tab 9*a* from Velcro tab 10 and allowing him to pull the goggle band 5 out of pocket 4. As the wearer continues to pull the goggle band 5 out of the pocket, the goggle band unfolds so that it comes to rest partially in front of the wearer's face, exposing the most forward position of goggle lens 7, which is embedded into the goggle band by means of a plastic or rubber encasement 7*a*.

Figure 3:

The wearer proceeds by continuing to pull the free end 5*a* of goggle band 5 outward and away from his face, and then wraps it horizontally across his face and attaches its free end to the opposite side of the hat as is shown best in FIG. 3. The free end of the goggle band is separably or detachably secured to the opposite side of hat 1 by means of male Velcro tab 9 attached to the underside of goggle band 5 mating with the female Velcro tab 14 affixed to the opposite side of the hat. If the wearer desires a tighter fit of the goggle band, he may place Velcro tab 9 further to the rear of Velcro tab 14. If he desires a looser fit of the goggle band, he may position Velcro tab 9 at a more forward position of tab 14.

As shown in FIG. 2, lines 15*a* and 15*b* define a non-permeable layer 15 in the same side of hat 1 on which pocket 4 and material 3 are located. Non-permeable layer 15 can be formed of a material that is non-permeable to fluids such as plastic, nylon or rubber that does not permit water or moisture to freely pass therethrough. When the lens 7 of the goggle band 5 is in its stored or resting position within pocket 4, and the wearer begins to sweat during physical activity, the perspiration leaving the wearer's forehead that passes into the hat is prevented by the non-permeable layer 15 from reaching the adjacent interior surface of lens 7. This can prevent the lens from fogging over, thereby allowing the wearer to have a clearer, unobstructed view through the lens when positioned over the face.

Area 16*a*, 16*b* of hat 1 is preferably made of a breathable material such as Gortex, cotton, or Primaloft, which does allow the passage therethrough of moisture and heat. By ventilating areas 16*a* and 16*b* and not ventilating the non-permeable area 15, the wearer's head is allowed to breathe and to expel moisture through the areas 16*a* and 16*b* but not through the non-permeable layer. The non-permeable layer 15 may be sewn or attached by Velcro tabs to the interior or exterior of the hat or may be secured to the hat by latches or hooks. The non-permeable layer may also be sewn in between an internal and external lining of a dual-layered hat. The non-permeable layer may also be in the form of a sprayed sealant or sprayed rubber material. This layer may also be formed by dipping the hat material into a liquid rubber, which, after drying coats the hat and creates a non-permeable layer.

Figure 4:
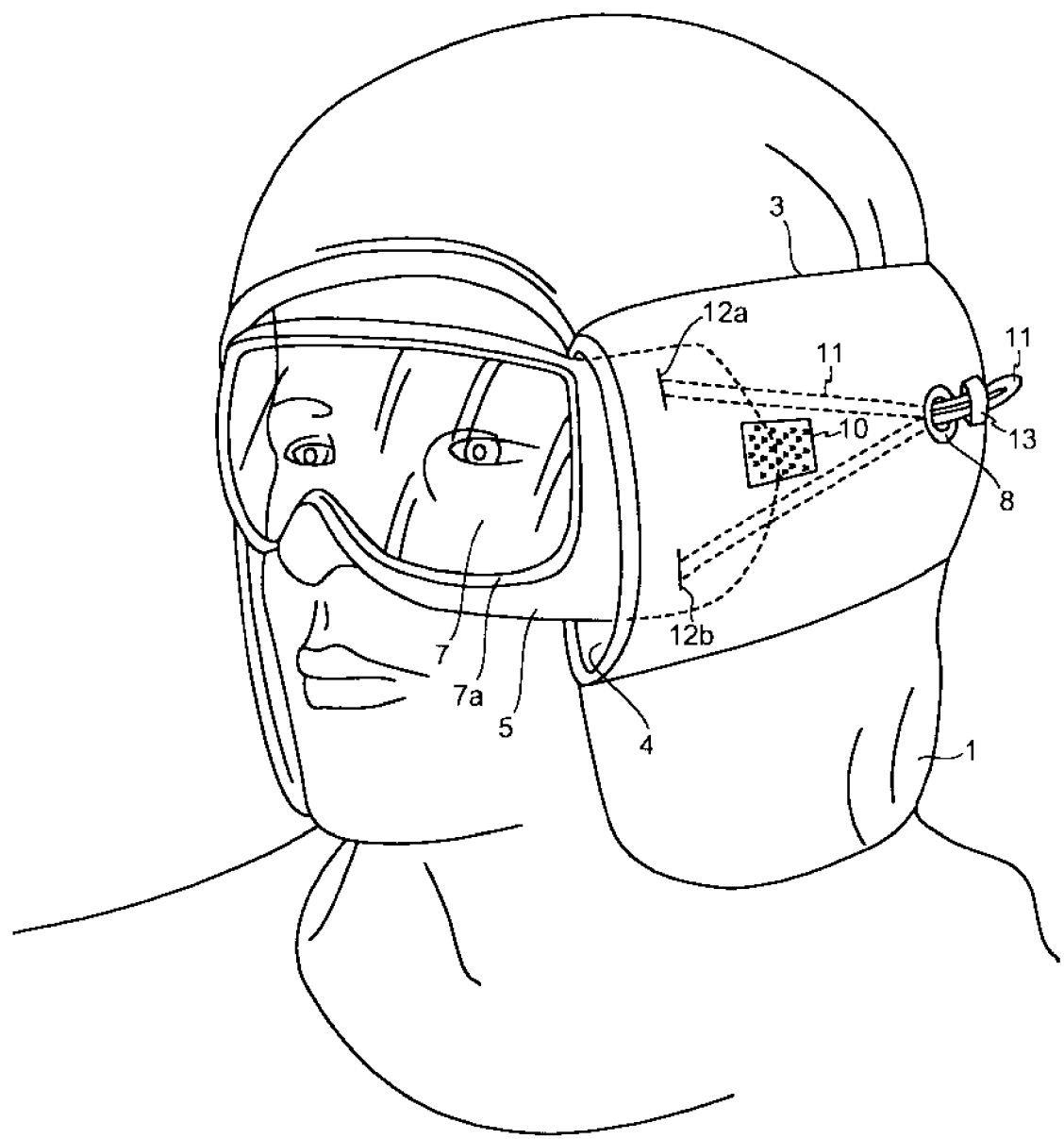

As can be seen in FIG. 4, the goggle band 5 is fully extended across the wearer's face and is separably attached at its free end 5*a* to the opposite side of hat 1. String 11 has been extended inward toward the front of pocket 4 and cord lock 13 acts as a stopper preventing string 11 from being pulled any further through the grommet opening 8, thereby preventing goggle band 5 from falling out of the pocket. Even in its fully extended position shown in FIG. 4, a part of the goggle band is retained within pocket 4.

It is also possible that pocket 4 and Velcro tab 14 be separably attached to hat 1 by Velcro or other known attaching means. If the goggle band is to be used with an open-faced helmet, the underside of pocket 4 and tab 14 may be coated with an adhesive. The wearer would peel off a protective backing and place the pocket and Velcro tab on the outer surface of the helmet.

If the wearer desires a yet tighter fit of the goggle band over his face, he may squeeze cord lock 13 and pull string 11 through cord lock 13, back and away from his head, thereby to pull the goggle band tighter around his face. Alternatively, the wearer may squeeze cord lock 13 while pulling goggle band 5 further out of pocket 4, which then pulls string 11 further into pocket 4, thereby allowing for additional slack in the string, which, in turn, results in a looser fit of the goggle band around the wearer's face.

To return the goggle band 5 to its original, stored position shown in FIG. 1, the wearer grabs the free end 5*a* of the goggle band 5 with one hand, and detaches Velcro tab 9 from Velcro tab 14. He then, with his other hand, grabs hold of string 11 by the slack that is left outside of cord lock 13, and then pulls retention string 11 out and away from his head, thereby threading string 11 outside of pocket 4 through grommet hole 8, which reactively causes goggle band 5 to be retracted into pocket 4 to its original rest position. The wearer then grabs hold of the free end 5*a* and folds it back over pocket 4, reconnecting it to Velcro tab 10 by means of Velcro tab 9*a*.

The wearer may either squeeze cord lock 13 and thread retention string 11 through it, as he pulls string 11 out and away from his head, or he may leave cord lock 13 in position and pull string 11 out and away from his head, thereby pulling cord lock 13 away from his head. If the latter is chosen, when goggle band 5 is back in pocket 4, the wearer may squeeze cord lock 13, and, while holding string 11, slide the cord lock 13 closer to material 3. It is also possible that excess slack of string 11 protruding out of pocket 4 may be stored in a built-in pocket. It is also possible to loop a Velcro tab around string 11, and then wrap the string around the wearer's head, and separably attach it to Velcro tab 14 on the opposite side of the hat.

Lens 7 may also be in the form of a holographic lens used to display holographic images, a 3-D lens used to watch three-dimensional movies, or in the form of a mixed reality or augmented reality lens. Goggle encasement 5 may also exist as a fully functioning virtual reality headset, and may be thicker in nature as typical virtual reality headsets are. If 3-D glasses are to be integrated it is also possible that the item of headwear may be made of plastic, paper, or cardboard to allow for cost efficiency in production. It is possible that the design can be integrated onto a baseball cap that is worn backwards. In this case, the wearer would turn the hat around so the brim is to the back of their head. He would then pull the lens out across his face and connect it to the other side.

In the case where goggle encasement 5f is used to hold a virtual reality headset, there may not be the need for pocket 4, as the headset may rest to the side of the wearers head in an exposed position, due to its inherent thickness.

Figure 5:
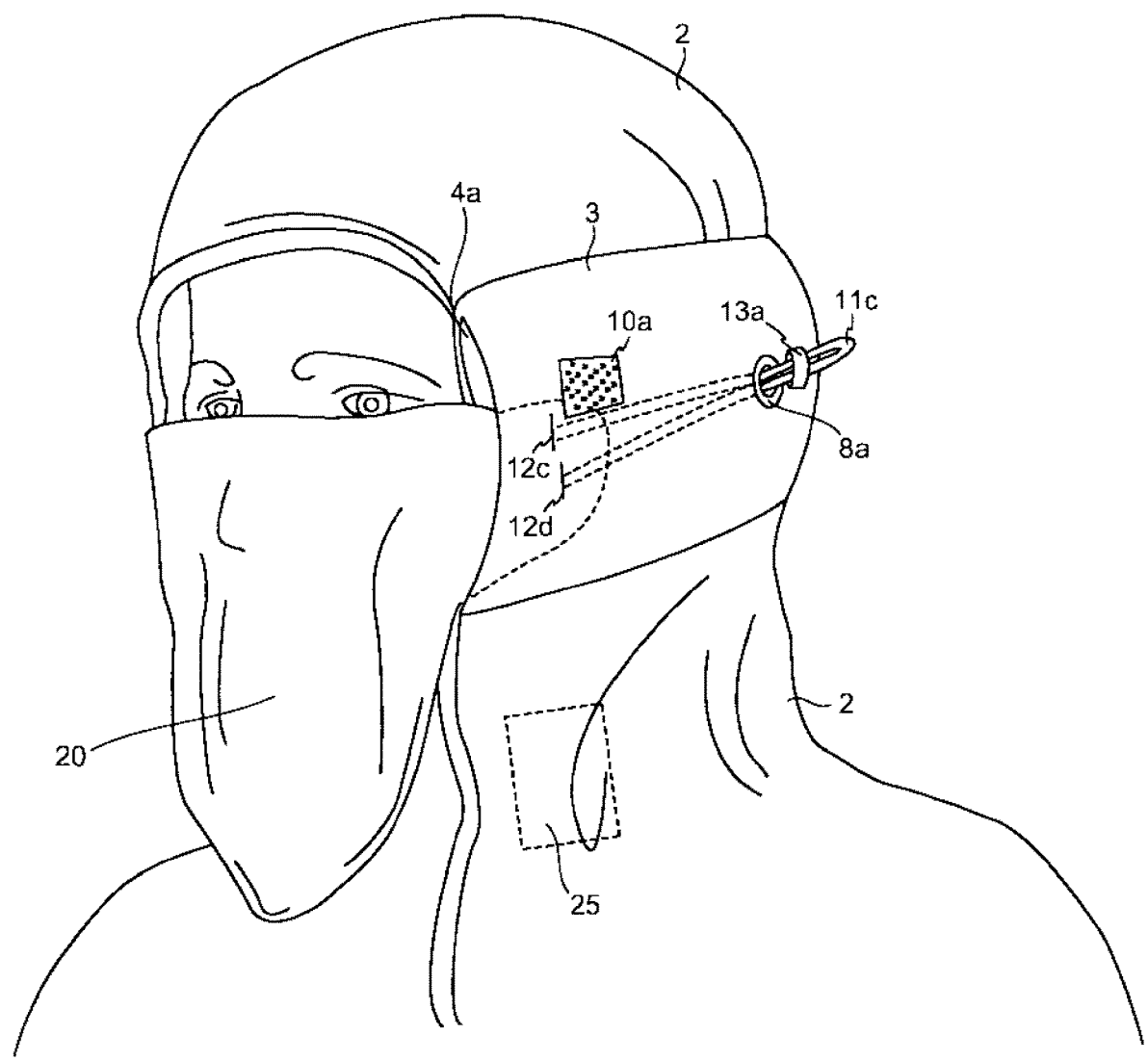
FIG. 5 illustrates a second embodiment as used in a hooded sweatshirt in which a bandanna is employed as an accessory.

FIG. 5 illustrates a second embodiment as used in a hooded sweatshirt in which a bandanna is employed as an accessory. The embodiment of the invention shown in FIG. 5 is similar to that shown in FIGS. 1-4 except that in place of a goggle band, a bandanna or scarf 20 is the accessory that is used in combination with a hood 2, which takes the place of the hat in the previously described embodiment. The size and shape of the bandanna are selected so that when it is deployed over the wearer's face, as seen in FIG. 5, it covers the wearer's nose, mouth, and cheeks.

A retention string 11c is fully extended within pocket 4a formed at one side of hood 2 so that cord lock 13a prevents bandanna 20 from falling out of the pocket. Although not shown in FIG. 5, it will be understood that the free end of the bandanna is separably secured to the (unseen) opposite side of the hood by means of a Velcro tab arrangement in manner that is similar to that described above in FIG. 3 for the goggle band. By tightening and loosening cord lock 13a the fit and snugness of the bandanna can be adjusted by the wearer also a previously described. It is possible that bandanna 20 may be embedded into the interior of a full-faced motorcycle helmet. It is also possible that bandanna 20 may be a disposable medical face mask and that hood 2 may be a disposable medical head covering.

As also shown in FIG. 5, a female Velcro tab 25 is attached to the internal side of hood 2. On the other side of the hood in relatively the same position, an internal male Velcro tab (not shown) mates with Velcro tab 25 to achieve a tighter fit of hood 2 around the neck. If desired, two pockets—one housing a goggle band and the other housing a bandanna—may be provided either on one side or on opposite sides of the hood so that both of these accessories may be deployed at the same time.

Figure 6:
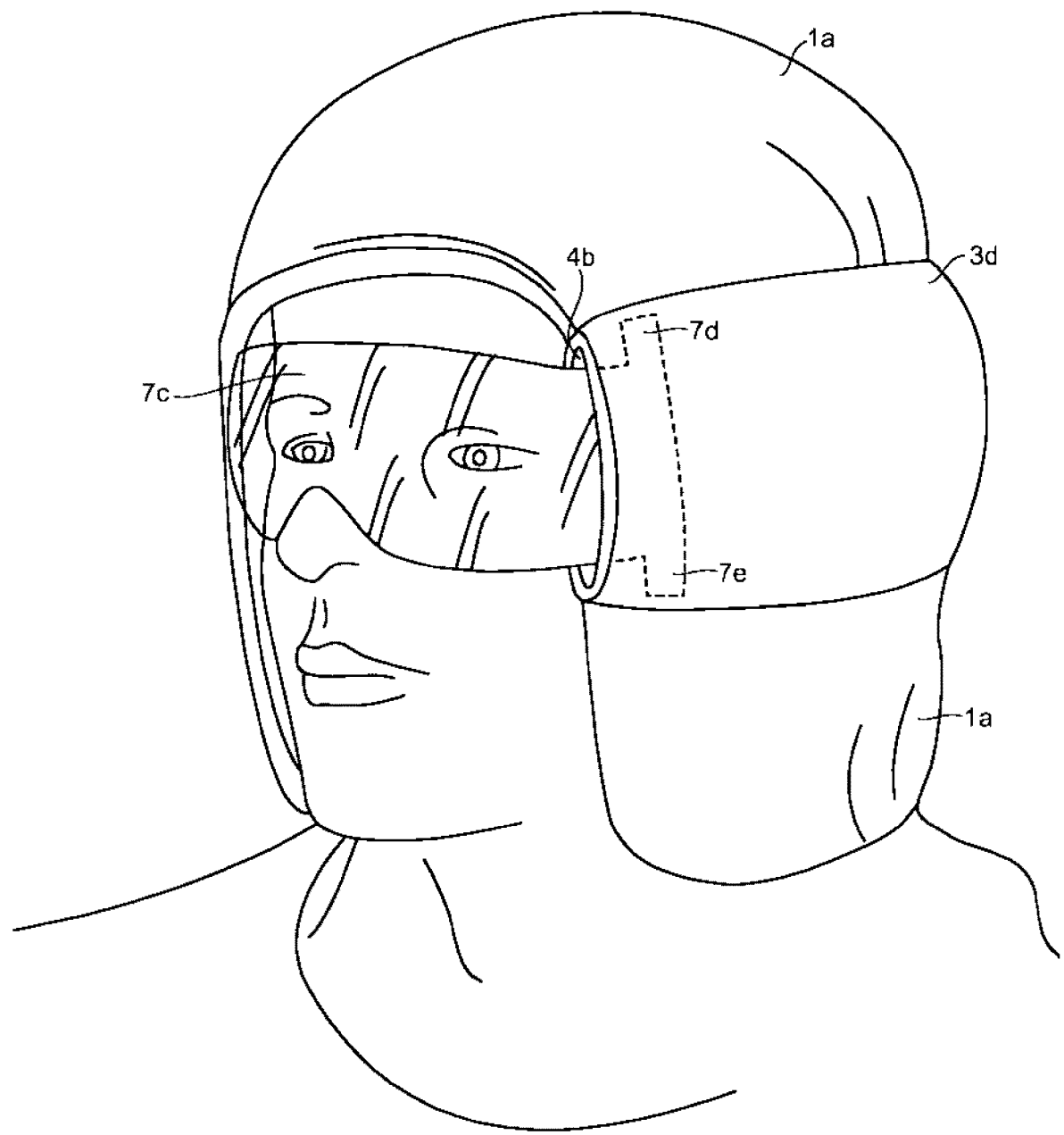
FIG. 6 illustrates a further embodiment where the accessory is a lens.

FIG. 6 illustrates a further embodiment where the accessory is a lens. In the embodiment of the invention illustrated in FIG. 6, a lens 7c covers the wearer's face when in use. Lens 7c is separably attached to the opposite side of hat 1a by means of a Velcro connection (not shown in FIG. 6). Lens 7c passes through a forward opening of pocket 4b, which is created by material 3d attached to the side of the hat. When not deployed over the wearer's face, lens 7c is retained in place within pocket 4b by means of extended lens tabs 7d and 7e secured to the inner end of the lens. Tabs 7d and 7e prevent the lens from sliding out of the pocket by engaging material 3d at the opening 4b since the size of opening 4b is less than height of the inner portion of lens 7c caused by the tabs 7d and 7e that extending upward and downward from the inner portion of the lens. Tabs 7d and 7e thus play the same retention function performed by retention string 11 in the embodiment of FIGS. 1-4. It is also possible that headwear 1a in FIG. 6 may be a disposable medical head covering, whereas lens 7c would then be a disposable plastic eye covering providing protection to one's face during medical procedures. Bandanna or scarf 20 in FIG. 5 may also be combined with headwear 1a, where it would rest below pocket 4b, so that lens 7c and bandanna 20 may be used at the same time to provide full facial protection during a medical procedure. Headwear 1a can also be made of paper or vinyl and may include anti-microbial materials, coatings, or structures that resist the transmission of microbes or other airborne particulates.

When the wearer wishes to end the use of the protective lens 7c, he manually releases the lens from Velcro tab 14 and manually pushes it back into the storage pocket. Lens 7c is adjustable at this point at which it connects to Velcro tab 14 at the opposite side of the hat. An adjusting device may also be added to material 3d or pocket 4b or to the allowed extension area of lens 7c, such as by the use of buttons or other types of closure devices on the interior of material 3d, that would be attached to the outer surface of the hat, inside and toward the front of pocket 4b. To close these connecting points would allow a shorter length of the lens to be released from the pocket, thereby allowing the lens to fit snugly over the face of a smaller person.

Figure 7:
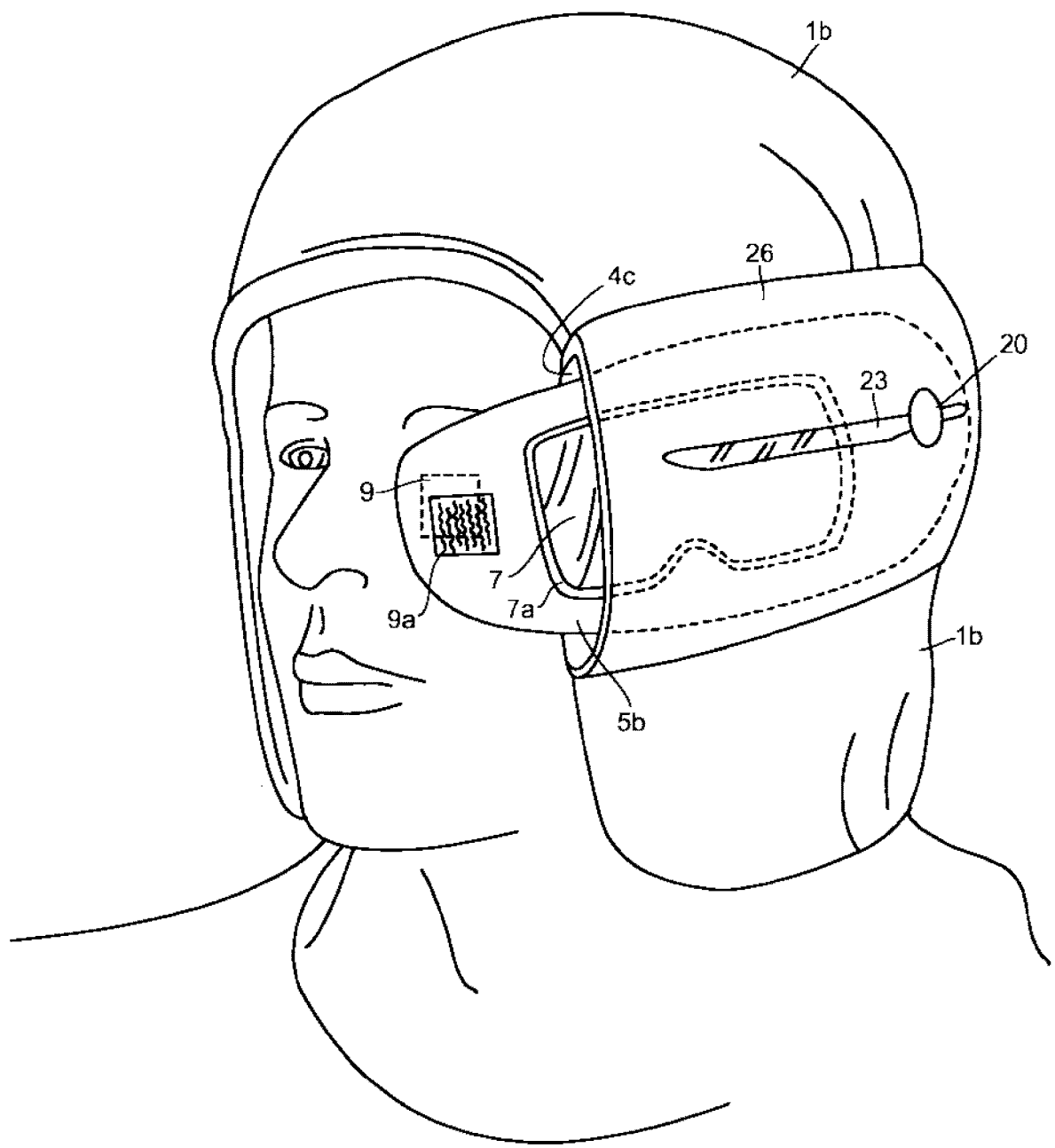
FIG. 7 illustrates another embodiment where the accessory is a goggle.

FIG. 7 illustrates another embodiment where the accessory is a goggle. In the embodiment of the invention shown in FIG. 7, an encasement 26 made of plastic, neoprene, or thermoformed plastic is attached to the outer surface of the hat to create a pocket 4c in which a lens or goggle band 5b is stored. The encasement 26 is preferably convex in shape. Goggle band 5b is attached to hat 1b by a knob 20, which is inserted through a slit or track 23 to encasement 26. Track 23 allows the goggle band to slide horizontally—front to back-in pocket 4c In use, the wearer grasps goggle band 5b at its free end, pulls it across his face, and attaches it to the opposite side of the hat as in the previously described embodiments. As this happens, knob 20 slides toward the front of pocket 4c toward the wearer's eyes along track 23. Further inward motion of knob 20 is prevented when the knob reaches its most forward position on track 23, which prevents the goggle band from falling out of the pocket. To retract goggle band 5b into the pocket, after use, the wearer first detaches the goggle band free end 5c from its separable attachment at the opposite side of the hat, and then takes hold of knob 20 with his other hand to slide the knob along track 23 back to its rearmost position in pocket 4c, which causes the goggle band to be pulled into its stored position within pocket 4c.

Figure 8:
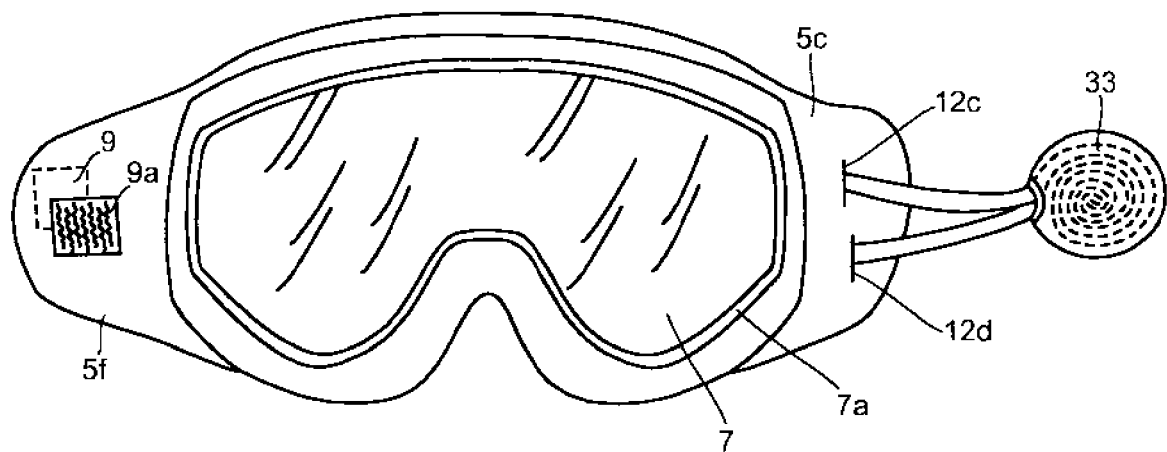
FIG. 8 illustrates an additional embodiment where the accessory is a goggle retractable by a reel mechanism.

FIG. 8 illustrates an additional embodiment where the accessory is a goggle retractable by a reel mechanism. In the embodiment of the invention shown in FIG. 8, a retention mechanism or wire begins at a point 12c on goggle band 5c and passes through a spring-loaded pull and reel mechanism 33. The wire then passes out of reel mechanism 33 and reconnects to goggle band 5c at a point 12d. The goggle band may also be used in any of the previously described embodiments by attaching reel mechanism 33 to the inside of the storage pocket. In use of the FIG. 8 embodiment, the wearer grabs area 5f of goggle band 5c and pulls it across his face to the opposite side of the hat. As this is occurring, the wire unwinds from reel mechanism 33 and extends through the pocket.

When the wearer attaches area 5f to the opposite side of the hat at Velcro tab 14, reel mechanism 33 locks in place and maintains the extended length of string 11 a constant. When the wearer no longer wishes the goggle band to be positioned over his eyes, he detaches area 5f from Velcro tab 14 and pulls area 5f out and away from reel mechanism 33, thereby to release the locking mechanism. The wearer then releases his hold on area 5f, which causes reel mechanism 33 to automatically recoil and rewind retention string 11 a back into reel mechanism 33, thereby to pull the goggle band back into the storage pocket.

Figure 9:
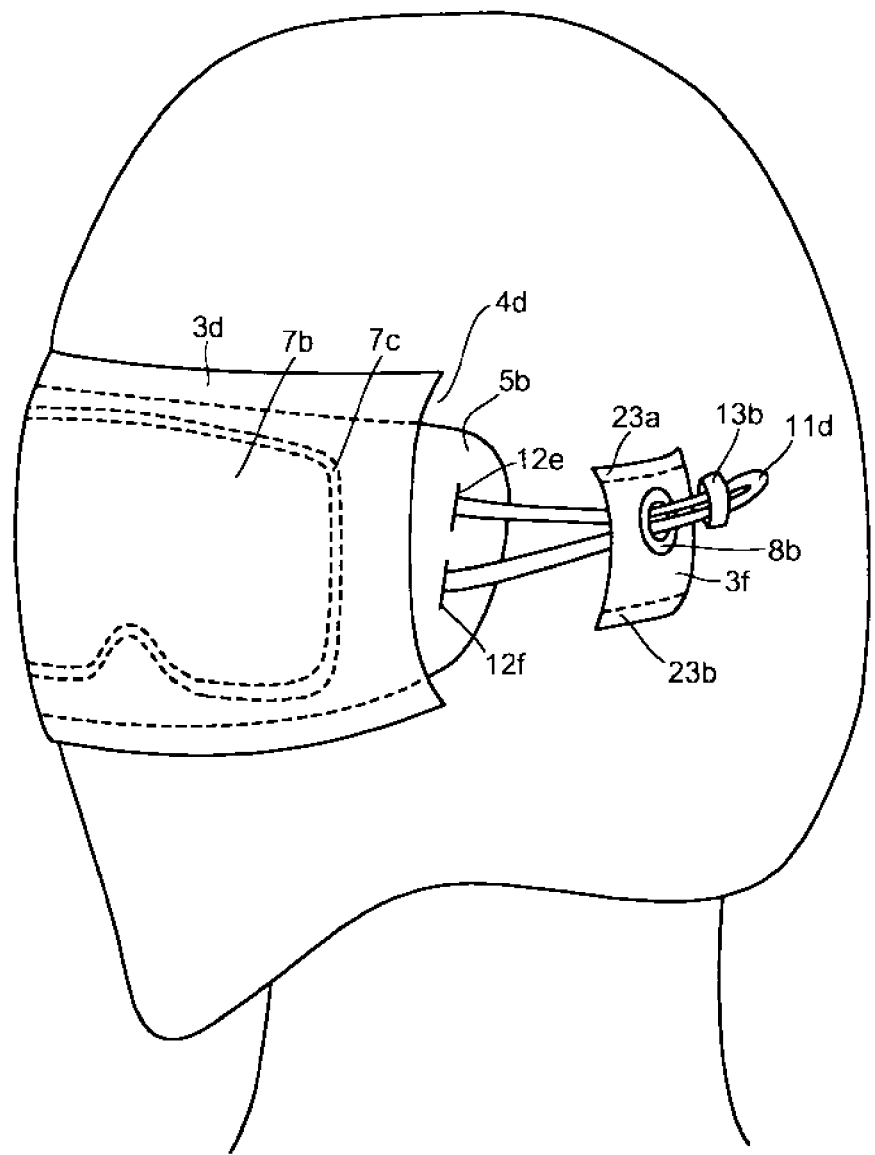
FIG. 9 illustrates yet another embodiment where the accessory is a goggle retractable by a string pulled through a fabric tab.

FIG. 9 illustrates yet another embodiment where the accessory is a goggle retractable by a string pulled through a fabric tab. FIG. 9 shows an alternate embodiment to that shown in FIG. 1, with the hat being viewed from the rear. Pocket 4b houses goggle band 5b by means of material 3d attached to hat 3. Goggle band 5b protrudes out of pocket 4d at the opening at its rear. A string 11d, attached to goggle band 5b at a point 12e, passes through a grommet 8b on a separate fabric tab 3f. Fabric tab 3f is sewn to hat 3 by an upper stitch 23a and lower stitch 23b. String lid then passes through cord lock 13b, loops back around passing through cord lock 13b, then through grommet 8b, and is reattached to goggle band 5b at point 12f. By positioning external tab 3f at a location further to the rear of hat 3, the wearer is allowed more leverage when he pulls goggle band 5b back into pocket 4b by means of string 11d. The position of tab 3f allows goggle band 5d to be pulled further back into pocket 4d.

As an alternate to string 11d, goggle band 5b may extend through pocket 4d to its rear in the form of a material band, which then may pass through a plastic ring or loop that would be used in place of grommet 8b. The excess, extended material from goggle band 5b would pass through this loop, change direction toward the front of the hat and be separably be attached by means of a Velcro tab, for example, to a designated area at the rear of the pocket. Excess material from goggle band 5b would pass through the loop and then through any known adjustable guiding mechanism. This arrangement allows for the lengthening or shortening of the excess material of goggle band 5b, thus allowing for an adjustable fit of the goggle band over the wearer's eyes. Excess, extended material from goggle band 5b or from string 11d may also pass out of pocket 4d at a slit or opening on the surface of material 3d at the rear of pocket 4d.

It is also possible to incorporate the reel mechanism 33 into the embodiment of FIG. 9 in which the reel mechanism would be placed between tab 3f and pocket 4b—either attached to hat 3 or left to hang loose. String 11d, beginning at point 12e, would pass out of pocket 4b, then through reel mechanism 33, through grommet 8b of tab 3f and then through cord lock 13b, where it loops around and passes back through grommet 8b, through reel mechanism 33, and is reattached to goggle band 5b at point 12f. Reel mechanism 33 may also be positioned external to tab 3f in a similar manner.

Figure 10A:
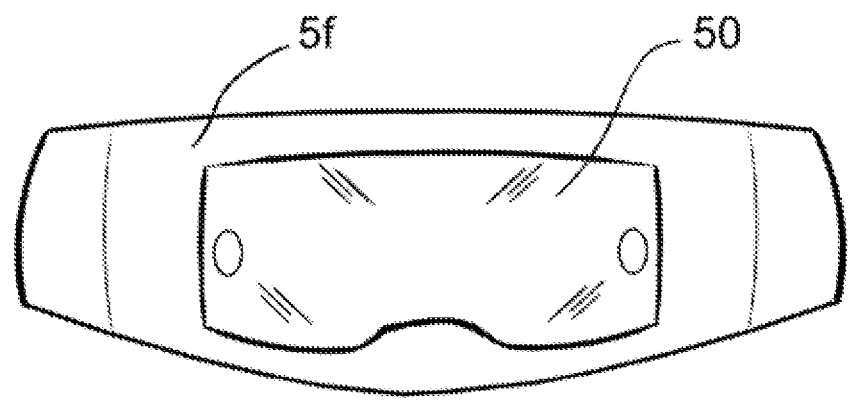
FIG. 10a illustrates a further embodiment used when the accessory is a smart phone holder.
Figure 10B:
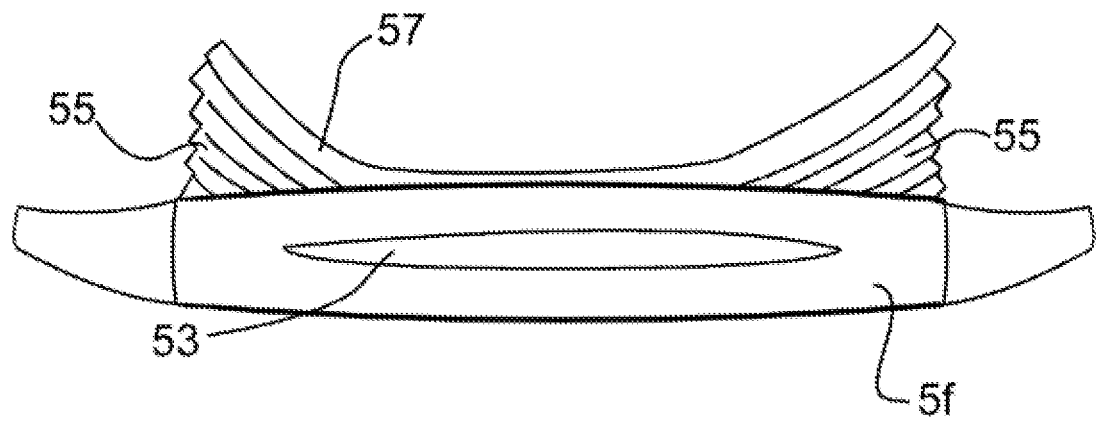

FIG. 10 illustrates a further embodiment used when the accessory is a smart phone holder. Encasement 5 may also exist as 5f in the form of a smart phone holder as seen in FIGS. 10a and 10b. 10a shows the smart phone holder, which can be made of neoprene or plastic. Here it holds smart phone 50, which can be brought across the user's face and used to show virtual reality media to the user. 10b shows a top view of encasement 5f, where opening 53 is used to receive smart phone 50. Here it is assumed that the storable pocket is situated to the right side of a user's head where it is brought across the face and attached to the left side.

Also shown as an extension of encasement 5f, are side guards 55 which connect the facial padding 57 to encasement 5f. Side guards 55 may be constructed of neoprene or fabric and used to restrict the entrance of light so that when the user has a smart phone situated over the eyes, viewing virtual reality programs, light will not enter and distort the media. Encasement 5 may also be constructed of an inflatable bladder.

Figure 11:
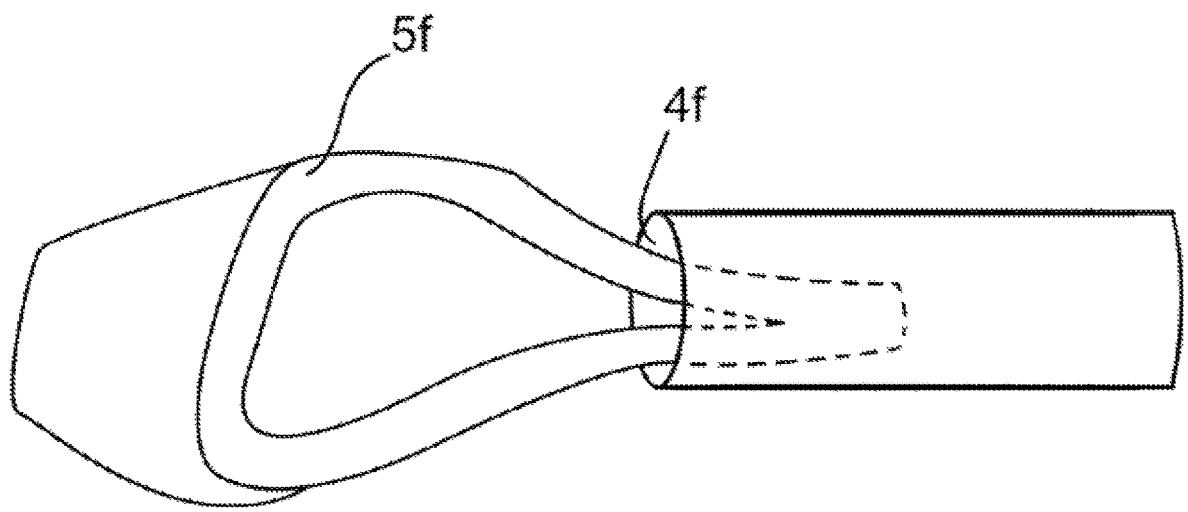
FIG. 11 illustrates yet another embodiment used when the accessory holder is compressed into the storable region of the main headwear portion.

FIG. 11 illustrates yet another embodiment used when the accessory holder is compressed into the storable region of the main headwear portion. It may not be desirable to store the smart phone to the side of one's head. In this case the user can remove smart phone 50, and place encasement 5f into pocket 4 (similar to that shown in FIG. 1. However encasement 5f may be bulky due to its natural size. In this case, it is also possible that encasement 5f is collapsible or foldable, so it can fit into a narrower or smaller pocket 4f as is shown in FIG. 11 (the main headwear portion is not shown)). It is also possible that there may be a mechanism attached to pocket 4f that would allow for compressing or tightening via means of a retention string or air pump. The air pump would suck out the air of the porous neoprene, reducing its size and the retention string would be pulled to make pocket 4f smaller, thus compressing the porous neoprene encasement 5f.

Figure 12:
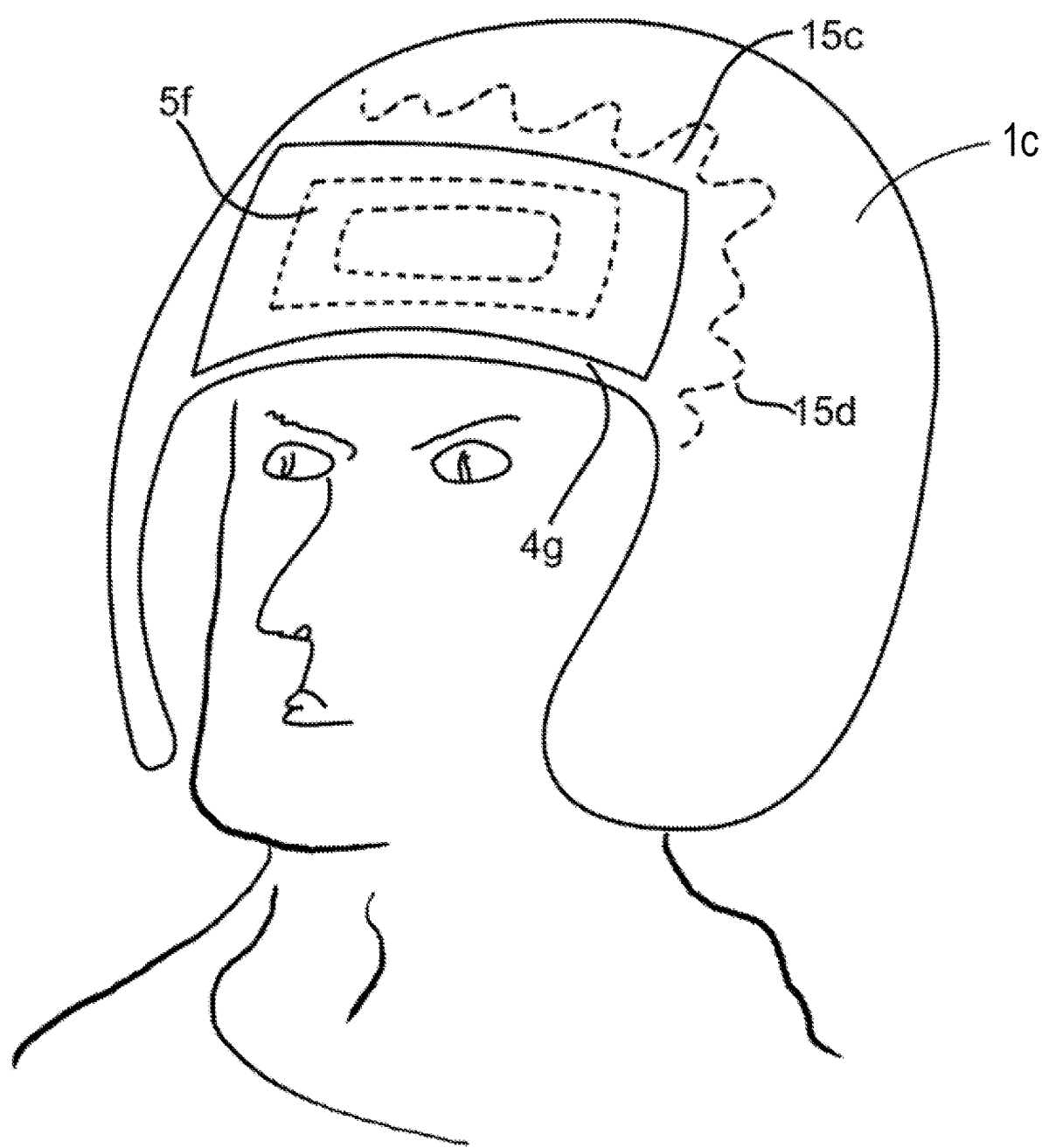
FIG. 12 illustrates yet another embodiment used when the accessory is stored within a region adjacent to the wearer's forehead.

FIG. 12 illustrates yet another embodiment used when the accessory is stored within a region adjacent to the wearer's forehead. Smart phones emit possibly harmful electromagnetic field (EMF) rays. When a smart phone is placed next to a user's head, it is possible for the head to receive the electromagnetic rays. When encasement 5f is being used to hold smart phone 50, and is stored in the storable region to the side of the head, an electromagnetic field blocker of standard sorts may be embedded into the item of headwear. The electromagnetic field blocker is depicted by line 15d surrounding the smaller dashed rectangle (representing the smart phone) inside the encasement 5f. It is also possible that this EMF blocker may also pose as the same non-permeable means to prevent moisture from reaching the stored accessory, thus preventing the fogging of the screen of the smart phone while protecting the user from EMF rays.

Furthermore, FIG. 12 shows non-permeable and EMF blocking area 15c outlined by area 15d surrounding the interior of pocket 4g, situated in the forehead region of headwear 1c. Pocket 4g houses smart phone encasement 5f without the smart phone. In use the encasement drops down from pocket 4g and covers the user's eyes. Headwear 1a may also exist as a headband or helmet. Material 15c may exist as one material, and serve two purposes: 1) to prevent moisture from reaching the stored accessory within pocket 4g, or 2) it can be used as an electromagnetic field blocker used to prevent EMF rays from the stored smart phone or virtually reality headset from reaching the user's head.

Figure 13:
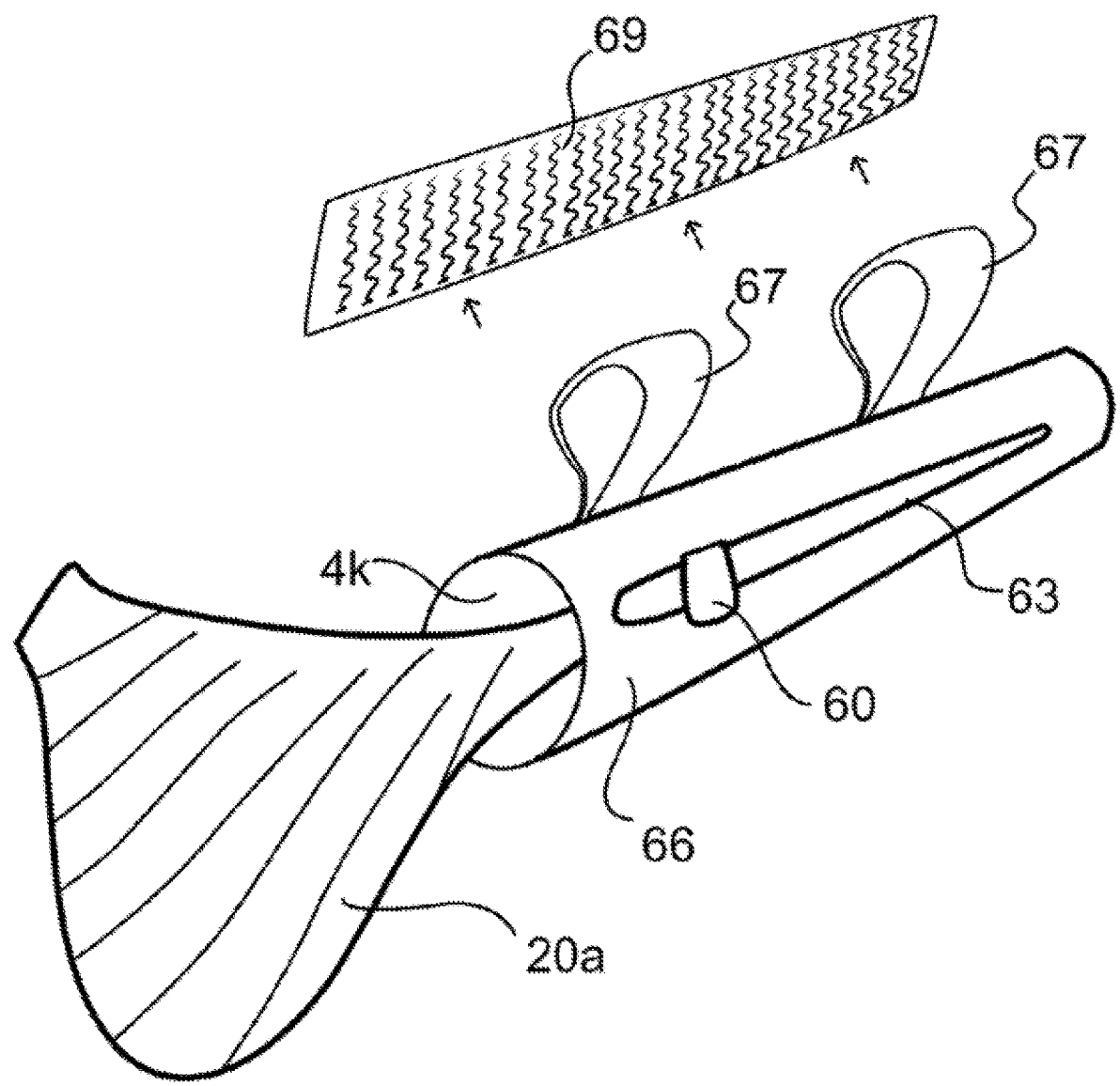
FIG. 13 illustrates a further embodiment used when the storable region is detachable from the main headwear portion.

FIG. 13 illustrates a further embodiment used when the storable region is detachable from the main headwear portion. FIG. 13 shows an embodiment similar to FIG. 5, but in this case, storable pocket 4k, which houses bandanna 20a is removable from a main headwear portion (not shown) by Velcro strip 69. Bandanna 20a is attached to outer rigid encasement 66 via means of knob 60, which penetrates outer encasement 66 through elongated horizontal slot 63. The wearer moves knob 60 back and forth to adjust the position of bandanna 20a within the storable pocket 4k or out of storable pocket 4k and across the user's face. It is possible that bandanna 20a is detachable from knob 60 so that it can be washed. It is also possible that outer encasement 66 may be removed from Velcro tab 69, turned backwards and connected to tab 69 again. In this case the user would pull mask 20*a* out of encasement 66, he's stretch it across his the rear of his head and connect it to the other side of the helmet, thus allowing the back of his head a form of sun protection.

Loops 67 are detachable from encasement 66 and can be used to attach the encasement to a construction or military helmet that typically have an interior meshing, lining, frame or webbing. Loops 67 would wrap around the messing, lining, frame or webbing and allow for encasement 66 to hang loose to the side of one's head, resting below the brim of the helmet. Loops 67 may also be tightened to secure a more snug fit of encasement 66. Loops 67 may also attach to the frame of an eyeglass or the frame of medical safety glass.

This design can be used with a motorcycle helmet or a snowboard helmet. Encasement 66 may also be tube like in nature, and curve to fit the contour of the helmet. It can either be attached to the exterior of a construction helmet or military helmet, or attached underneath the brim, to the interior of the helmet, allowing for encasement 66 to be kept out of sight.

It is also possible that encasement 66 as seen in FIG. 13, may be attached, glued to, or sewn to a helmet covering, whereas the mask 20*a* would be pulled from pocket 4*k* and attached to the other side of the helmet covering. This can be done for helmet coverings that are used for snowboard helmets or military helmets. In this case, the encasement 66 may also be made of fabric or a thermos-formed plastic. The entire helmet covering along with encasement 66 may be removed so that it can be washed.

It is also possible that mask 20*a* may be constructed of a noise canceling or noise buffering material, which may also have a built in microphone attached to Bluetooth mechanism, which is connected to a smart phone, ear phones or an ear piece, so that the user may attach tabs 67 to an eye glass, pull the mask across his face and speak into the mask. This would allow him to have a private phone conversation in the presence of others, as the mask will buffer his words. Case 66 may also be directly attached to a Bluetooth earpiece and stretched across the wearer's face.

It is further possible that mask 20*a*, may exist as a medical safety mask that would attach by loops 67 to a medical safety eyeglass to be worn during medical procedures. Loops 67 may be open or constructed in the form of hooks, so that encasement 66 hooks on to the medical safety glass. It is also possible that mask 20*a* maybe attached to a cylinder like holding mechanism that wraps around the arm of the eyeglass frame, as we will see in FIG. 18. Further more, it is also possible that the inside of encasement 66 has a covered adhesive, so that the user could peel off the cover, exposing the glue and then stick encasement 66 to a hat, a protective hood, a medical head covering, the arm of a medical safety glass, their hair or their face, where he would then pull the mask across his face and attach it to the other side. It is also possible that the mask as well as the entire contraption is disposable.

Lastly, mask 20*a* may be constructed of a paper like material that may be folded with multiple folds and stored to the side of ones head without an encasement or covering like 66. Between the many folds, there would exist dots of glue or adhesive that allows the mask to fold and remain stored in a smaller area then if it were fully opened or spread out. When folded the mask would then have a rigid internal side made of paper, plastic or cardstock, which would have an area coated with and adhesive, which would be covered until the user is ready to use the mask. In use, he would peel off the cover, stick the adhesive to a head covering or safety glass arm, and then pull the mask across his face attaching it to the other side of the head covering or safety glass frame. As he does this, the glue holding the foldable mask together will tear apart, thus allowing the mask to spread across his face. This would work well for a medical use situation. It is also possible the paper mask may be designed or cut so that in only covers the users nostrils when spread across ones face.

Figure 14A:
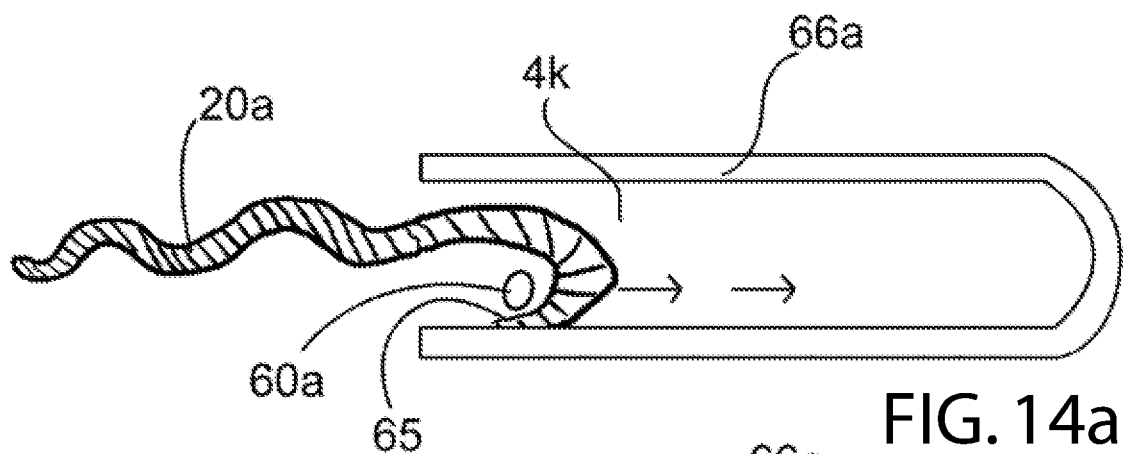
FIG. 14a illustrates yet another embodiment used when the mask is stored within the storable region.
Figure 14B:
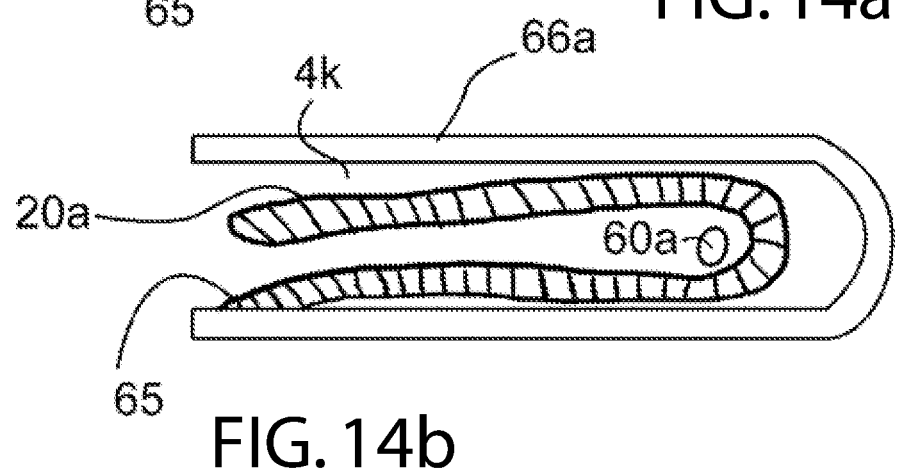
FIG. 14b illustrates the embodiment of 14a when the mask is completely withdrawn into the storable region.

FIG. 14 illustrates yet another embodiment used when the mask is stored within the storable region. FIG. 14 shows an embodiment similar to FIG. 13, but in this embodiment the size of storable pocket 4*k* is reduced. FIG. 14 is shown as a sectional view to illustrate the mask 20*a* being drawn into the pocket 4*k*. As shown in FIG. 14*a*), the mask 20*a* is attached to encasement 66*a* at point 65. Knob 60*a* protrudes through the top (not shown) of plastic encasement 66*a*, and can be moved back and forth along a track (not shown) to change the position of bandanna 20*a* within pocket 4*k*, similar means as is shown in FIG. 13 by knob 60 and track 63. This is shown in FIG. 14 *b*) where the mask 20*a* is completely withdrawn into the pocket 4*k*.

Having the mask 20*a* affixed at the point 65 and extending partially around the knob 60*a*, allows for mask 60*a* to be retracted into plastic storable pocket 4*k* without taking up the full space or length of mask 20*a*, as the mask 20*a* is now folded in half as shown in FIG. 14 *b*). This also allows pocket 4*k* and plastic encasement 66*a* to take up less space when attached to a helmet, an eyeglass, or an item of headwear. Encasement 66*a* can be tubular in shape, with a slot (not shown) to allow the knob 60*a* to slide along the length of the plastic encasement 66*a*.

Figure 15:
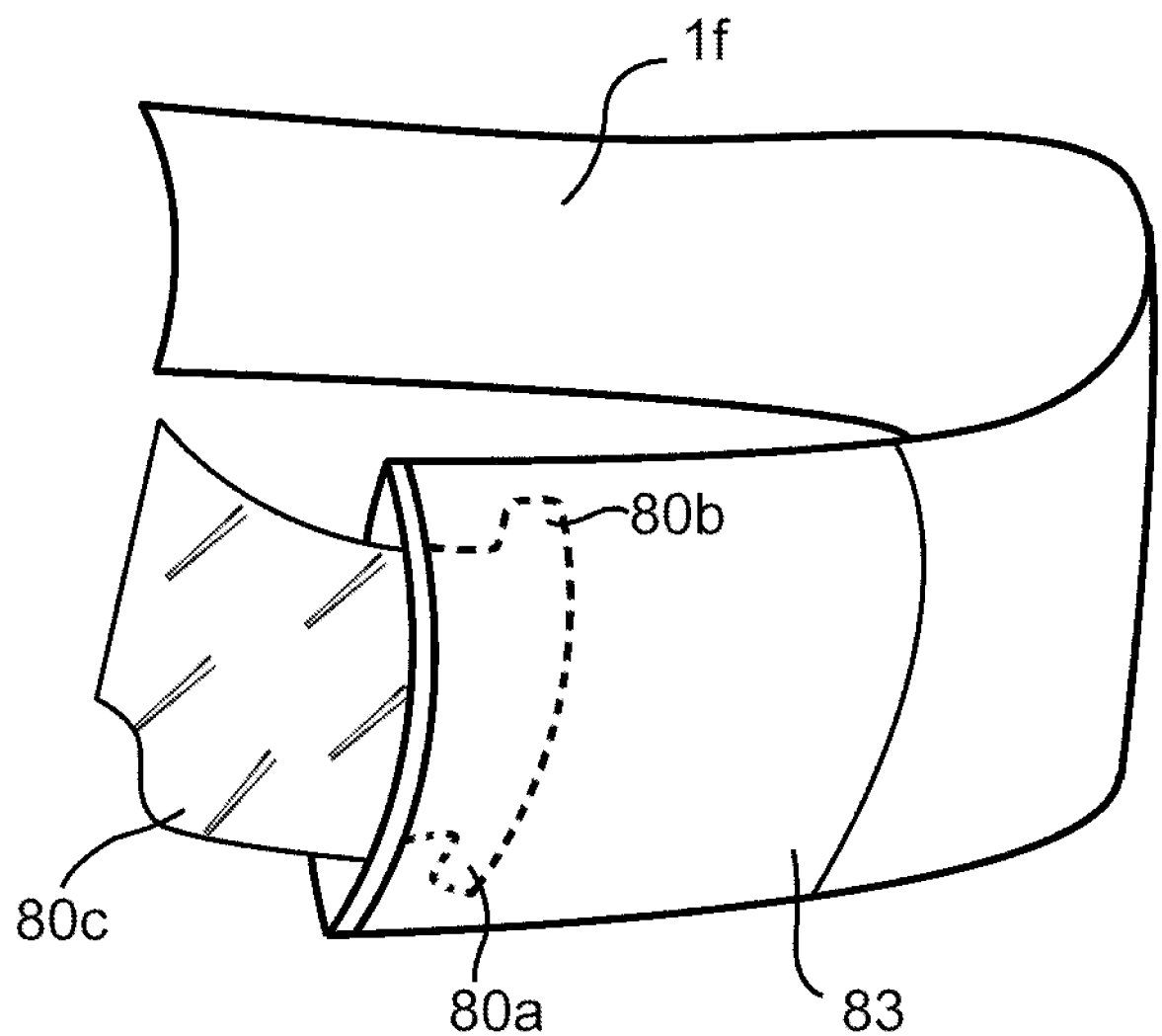
FIG. 15 illustrates yet another embodiment used when a portion of a holographic lens is stored within the storable region.
Figure 16:
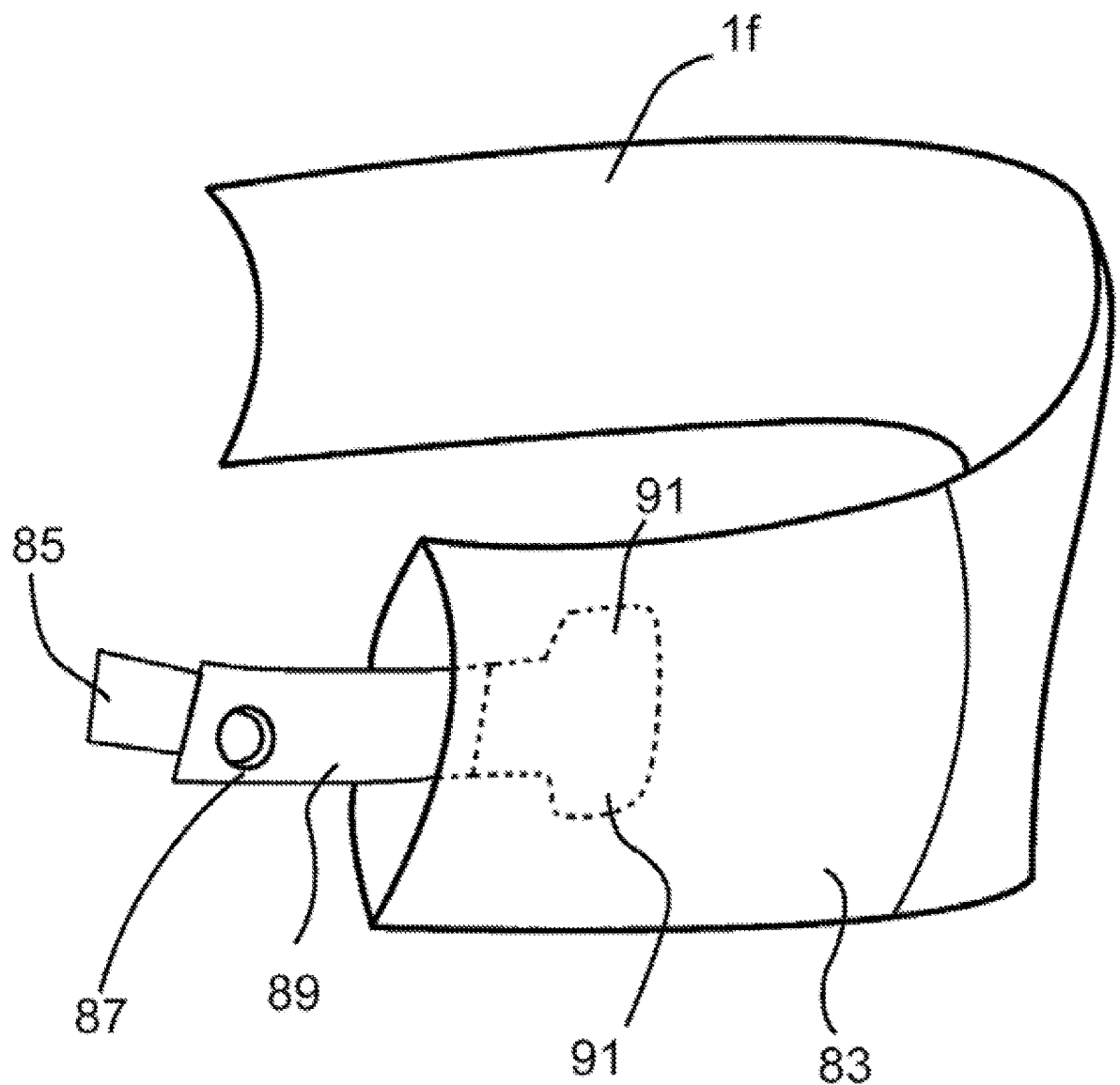
FIG. 16 illustrates yet another embodiment of the invention used when an optical head-mounted display is stored within the storable region.

FIG. 15 illustrates yet another embodiment used when a portion of a holographic lens, a mixed reality lens, or an augmented reality lens is stored within the storable region. FIG. 16 illustrates yet another embodiment of the invention used when an optical head-mounted display is stored within the storable region.

FIG. 15 shows an embodiment similar to FIG. 6 but in this design lens 80*c* is held into pocket 83 of headband if by extended tabs 80*a* and 80*b*. Headband if is an open headband, which holds its shape when made of a semi-rigid plastic or thermoformed plastic. Headband if may be rigid, semi rigid, or soft in nature. A camera may also be embedded into lens 80*c*.

The lens 80*c* can be, for example, half the size of lens 7*c* in FIG. 6, so that lens 80 will only cover one of the wearer's eyes. This can be relevant for designs that are used to incorporate holographic lenses or an optical head-mounted display or Goggle Glasses as shown in FIG. 16. Here a visual overlay 85 is connected to the head-mounted optical display 89, which is being held into pocket 83 of headwear if by means of extended tabs 91. In use, the wearer can pull head-mounted optical display 89, which can include camera 87, from its storable region and slide the head-mounted optical display 89 over a left eye. When finished, the user can slide head-mounted optical display 89 back into pocket 83. Headwear if may also be made of a fabric, plastic, thermoformed plastic, or a semi rigid thermoformed plastic.

Figure 17:
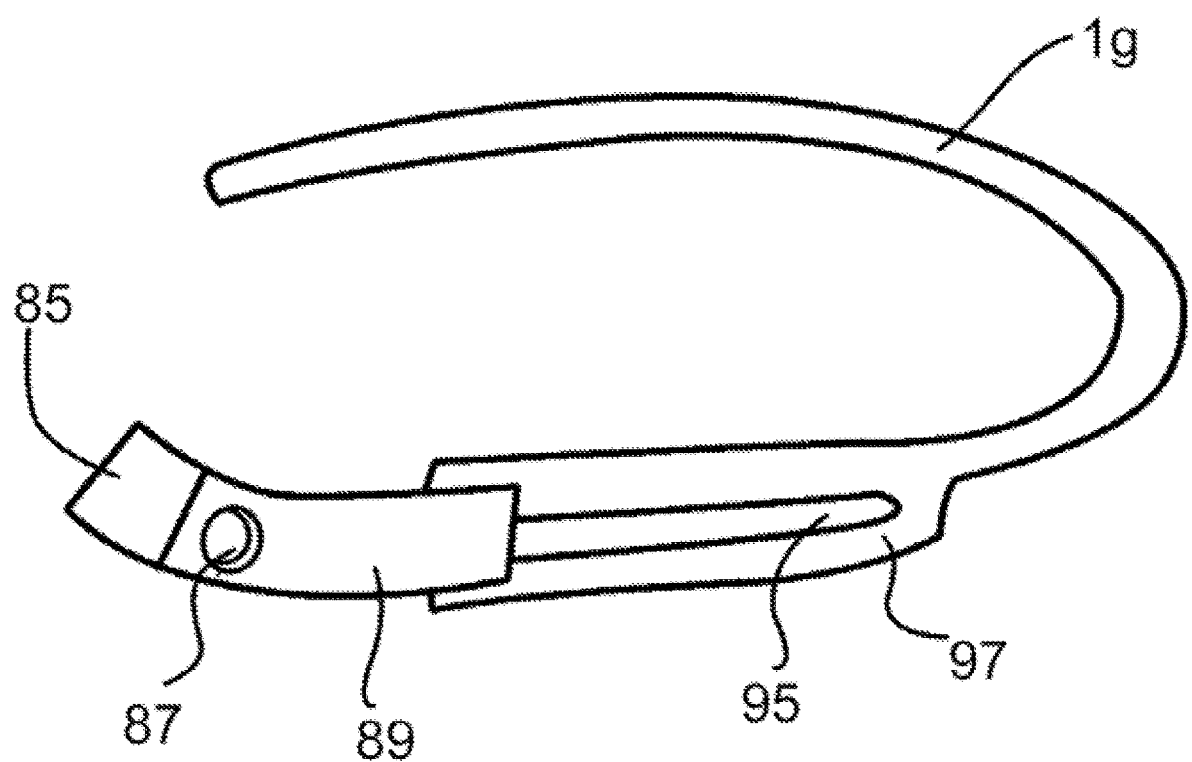
FIG. 17 illustrates another embodiment of the invention where an optical head-mounted display is stored to a storable region.

FIG. 17 illustrates another embodiment of the invention where an optical head-mounted display is stored to a storable region. FIG. 17 shows plastic headband 1*g* which can wrap around the rear of the users head and held in place by the structure of the molded plastic. Side mount 97 houses a horizontal elongated track 95, which can hold head-mounted optical display 89 (consisting of camera 87 and visual overlay 85) to headwear 1*g*. In use, the wearer slides head-mounted optical display 89 over the left eye to use camera 87 as well as visual overlay 85. When finished, the user can slide display 89 back into the storable region on side mount 97 via means of track 95. This design may also be embedded into a semi rigid headband, a winter beanie, or a ball cap. Side mount 97 (or just the front portion) along with head-mounted optical display 89, may also be attached to the side arm of sunglasses or eyeglasses. Furthermore track 95 may be built into the arm of eyeglasses so that optical display 89 can slide along track 95 so that it can be positioned over the wearer's face or stored to the side of the eyeglasses.

Figure 18:
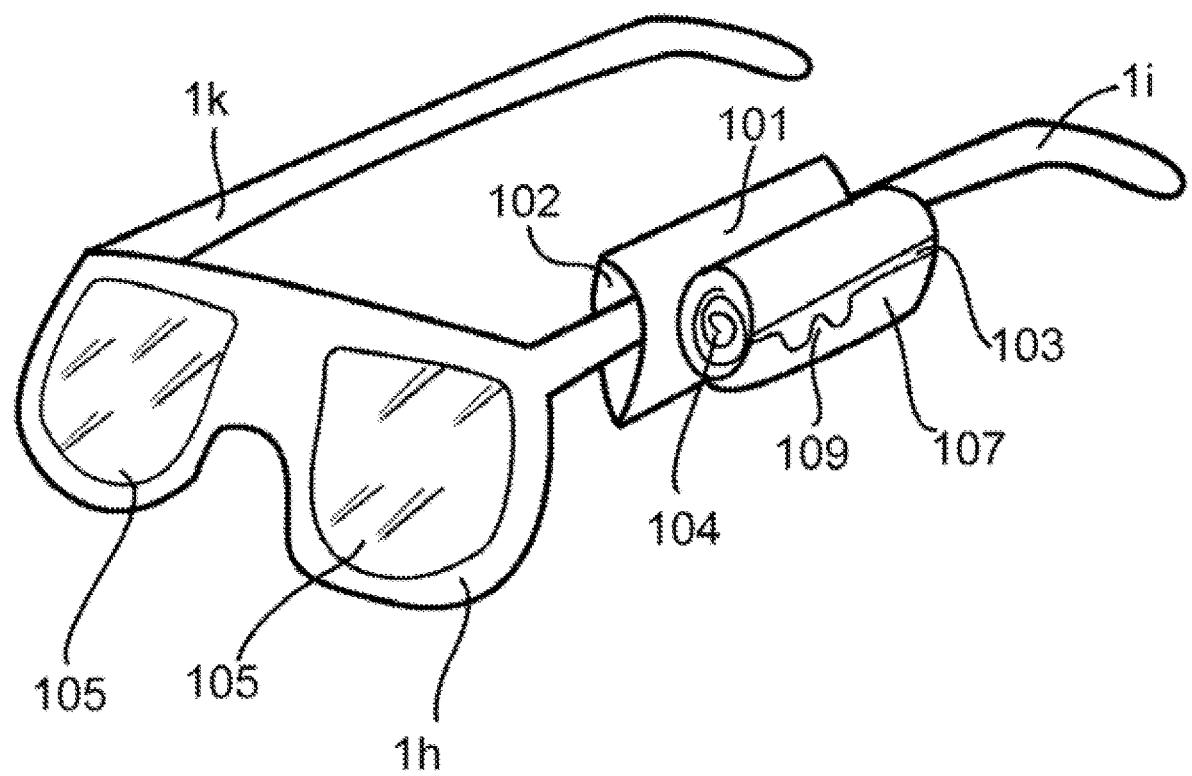
FIG. 18 illustrates yet another embodiment of the invention where a retractable lens is stored in a capsule.

FIG. 18 illustrates yet another embodiment of the invention where a retractable optical lens, an augmented reality lens, a holographic lens or a sunshade is stored in a capsule. FIG. 18 shows eyeglasses 1h with side arms 1k and 1i as well as left and right lenses 105. Side arm 1i travels through hole 102 of side pocket 101 to house sunshade 104, which can be rolled into a horizontal cylindrical capsule 107. Sunshade 104 protrudes capsule 107 at opening 103.

In use, while wearing typical eyeglasses, when the user desires to have protection from the sun or to engage his augmented reality lens, he takes capsule 105 and rotates it into a vertical position as seen in FIG. 19. Capsule 107 is attached to pocket 101 by means of track 110. When capsule 107 is vertical, the user can then grab tab 109 and pull tab 109 across eyeglass 1h, unraveling sunshade 104 from capsule 107 at opening 103. When sunshade or lens 104 completely covers eyeglass 1h, the sunshade 104 can attach to the side arm 1k by means of tab 109, protecting the eyes from the sun or allowing the user to have an augmented reality experience. When sunshade or lens 104 is no longer needed, tab 109 can be detached from side arm 1k and pushed back into capsule 107. Tube 107 may be large or small in nature, which would allow for a small sunshade or a large sunshade to be stored. Opening 102 may consist of a neoprene or other elastic material, which can provide a snug fit around side arm 1i. Sun Shade 104 may also consist of a camera or a microscopic camera and projector combination in the case where it is used as a mixed reality lens. The user would pull the lens over his face and engage in a mixed reality experience.

Capsule 107 may also house a small camera or video camera affixed to a retention string or an electrical cord that is retracted into the capsule by a pull and reel mechanism as seen in FIG. 8. Bluetooth may connect this camera to the user's smartphone. In use the wearer would pull the camera from the Capsule 107 out and away from his head, take pictures or videos of the surrounding area, or take pictures of himself, which would then transfer directly to his smart phone. When he is finished taking pictures, the wearer would then pull the camera further away from his head, which causes the reel mechanism unlock, and then automatically recoil and rewind the retention string back into reel mechanism or Capsule 107. This camera may also have multiple lenses or surfaces that allow it to record in multiple angles so that the footage may be integrated into a virtual or augmented reality experience. It is also possible that the retention string attached to the camera may be retracted directly into the hollow side arm of the eyeglass frame. In this case the camera may rest or exist in the upper left (wearer's left) corner of the left lens 105. There may also be a button situated on arm 1i that when pressed, it automatically retracts the retention string back into the capsule 101 or into the frame 1i.

Figure 19A:
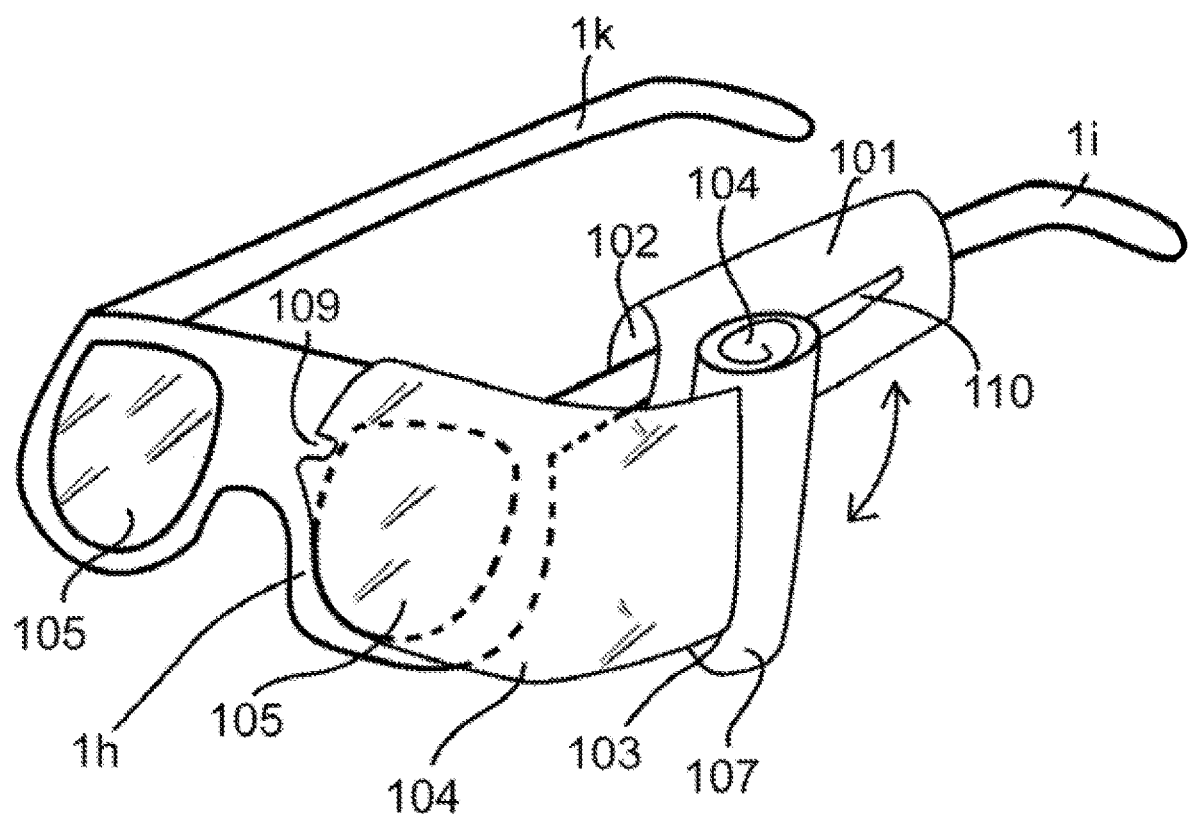
FIG. 19a illustrates FIG. 18 in use.
Figure 19B:
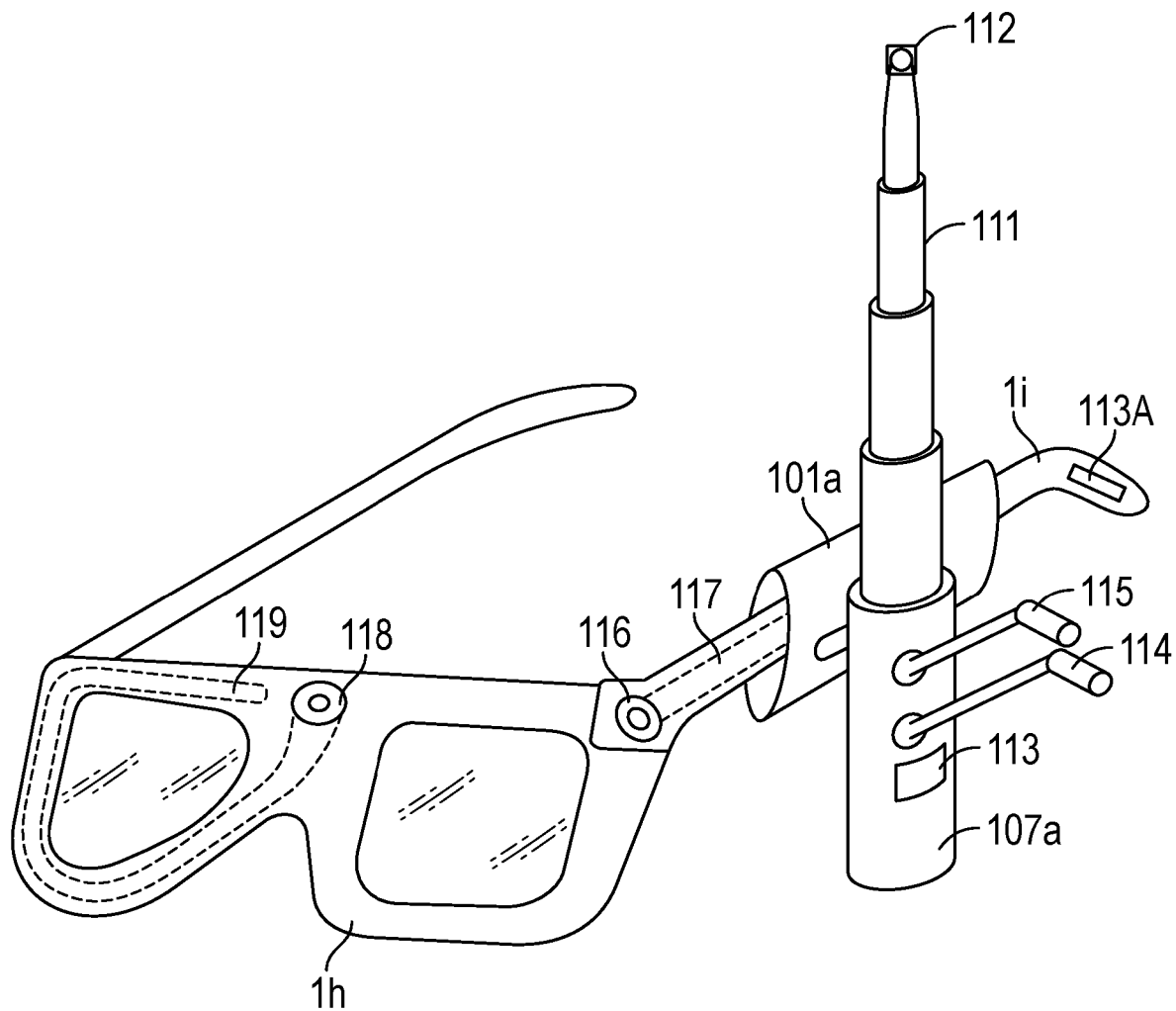
FIG. 19b illustrates FIG. 19 when used with a camera attached to a retractable rod.

It is also possible that a capsule 107 may house a cylindrical extendable rod like mechanism or a collapsible rod similar to a collapsible antenna that would have a camera or video camera or a multitude of cameras or video cameras situated at the end of or on the tip of the antenna as is seen in FIG. 19b.

In use the user would pivot capsule 107a so that it is vertical to one's head. He would then raise the antenna or cylindrical extendable rod 111 above his head and take pictures or video of his surroundings with camera 112 by pressing a button situated on the eyewear (not shown) which would then transfer the images or videos wirelessly back to his smart phone or to an augmented or virtual reality lens. When he is finished taking pictures or video he would then manually retract the camera and the rod back into capsule 107a. He may also press button 113, which would automatically retract the rod into case 107a.

Since capsule 107a is pivotal in regards to encasement 101a, he may point the camera or cylindrical rod in any direction at any angle or direction, horizontally, vertically from the wearer's head. This cylindrical rod may also have a cranking mechanism 113 that when manually turned would recoil or retract the cylindrical extendable rod back into capsule 107a. He may also turn the wheel in the opposite direction in order to raise or extend the cylindrical extendable rod out of capsule 107a away from his head.

When antenna 111 is fully extended above his head, he may use cranking wheel 115 to control the direction of camera or video camera 112. In use he would turn wheel 115, which would cause camera 112 to turn 360 degrees. The footage used from the camera, multitude of cameras, or video camera turning 360 degrees could be integrated into a virtual reality or augmented reality medium. The camera could also be used for military purposes so that a soldier, while taking cover, could raise camera 112 higher than his bunker to see what dangers are present. He would then crank wheel 115 to scan his surroundings, which could then deliver a visual to his smart phone or to any mixed reality lens that has been described in this application. Encasement 101a or capsule 107a may be entirely removable from arm 1i, so that that they can be used on other eyeglasses or sunglasses. Encasement 101a may also have a clip so that in can clip onto eyeglass arm 1i or any other eyeglass or item of headwear.

It is also possible that the extending and turning of the cylindrical extendable rod 111 and camera 112, may be done electronically or wirelessly via means of a remote control or by an app or program on the user's smart phone. The smart phone or remote control could also control the camera or video cameras.

Also shown in FIG. 19b is camera 116, which is attached to an encased extension mechanism or rod 117 built into the hollow arm 1i of eyeglass 1h. In use the wearer would grab camera 116 and extend it out and away from his face, similar to how rod 111 extends from encasement 107a. Rod 117 may constructed of plastic, metal or entirely of a moldable or bendable, semi rigid rubber or plastic which could be manipulated to hold its shape or position by the user when extended. The user may also press button 113a to automatically retracted rod 117 back into arm 1i.

Also shown in FIG. 19a is camera 118, which is attached to rod 119, which is encapsulated into the hollow structure of eyeglass 1h. In use the user would grab camera 118 and pull it out an away from his face as has been described. When the camera is no longer needed he would manually push it back into its original position, where eyeglass 1h would then house rod 119.

Figure 20:
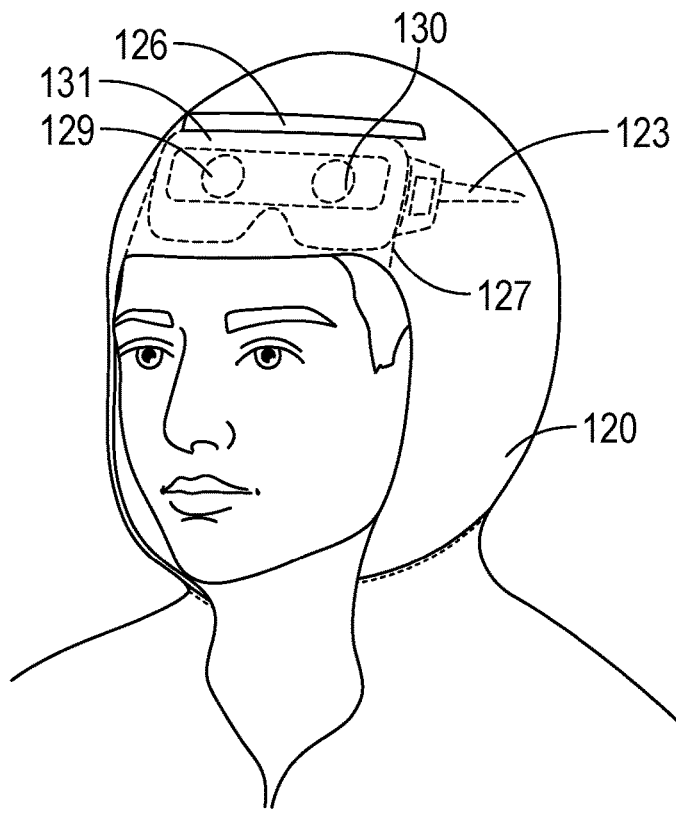
FIG. 20 illustrates another embodiment of the invention were the smart phone holder is built into the upper portion of a hood.

FIG. 20 shows a hood 120 with an opening 126, which houses a neoprene foam rubber smart phone holder 131 inside of pocket 127. Lens 129 and 130 are built in to a layer inside of pocket 127 to facilitate a virtual reality experience when the user takes his smart phone, inserts it into pocket 127 via means of opening 126. He then pulls the entire hood 120 down over his face so lenses 129 and 130 are positioned over his eyes in front of the viewable screen of his smart phone, allowing for a split virtual reality window to be viewed in the proper manner.

He may pull string 123 from the rear to tighten the fit of hood 120. Smart phone holder 131 may be made of plastic, foam rubber or of an inflatable bladder. Holder 131 does not leave pocket 127, and it is only allowed to cover one's face when the user pulls hood 120 down over his eyes.

Lenses 129 and 130 may also be situated or built in or attached in front of smart phone holder 5f as is seen in FIG. 10.

Figure 21:
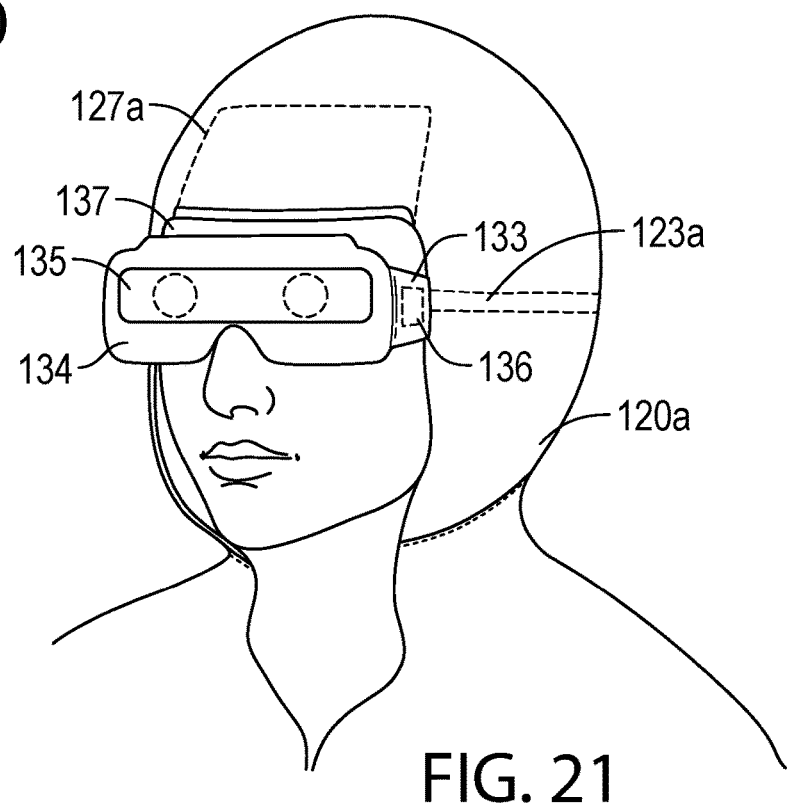
FIG. 21 illustrates FIG. 20 in use, when the holder is positioned over the user's eyes.

FIG. 21 shows a similar embodiment to FIG. 20, but in this drawing smart phone holder 134 holds smart phone 135 and is folded downward along line 137 from the inside of hood 120a, over the wearer's face. Wing 133 of smart phone holder 134 attaches holder 134 to hood 120a by means of Velcro tab 136. Region 127a depicts the area where smart phone holder 134 is stored when not in use. Region 127a may also outline an internal pocket, which can be used to store smart phone holder 134. Retention string 123a is used to tighten the fit of hood 120a. In place of smart phone holder 134, a mixed reality lens may be substituted in its place, where it would also pivot along area 137 into and out of hood 120a.

Figure 22:
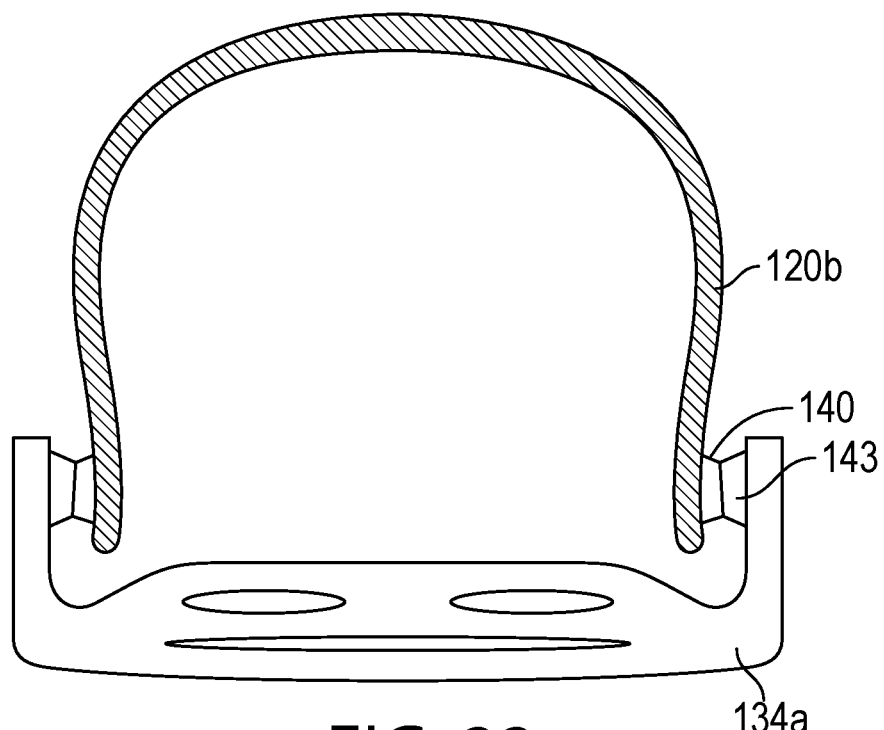
FIG. 22 illustrates an embodiment where a smart phone holder is attached to the outer surface of a hood.

FIG. 22 shows a top view and horizontal cross section of smart phone holder 134a as a separate unit, which is attached to hood 120b, by means of Velcro tabs 140 and 143. Smart phone holder 134a may also be constructed of an inflatable bladder. In the case where smart phone holder 134a is inflatable, it may be detached from hood 120b, deflated, and stored in a pocket within the hooded sweatshirt.

Figure 23:
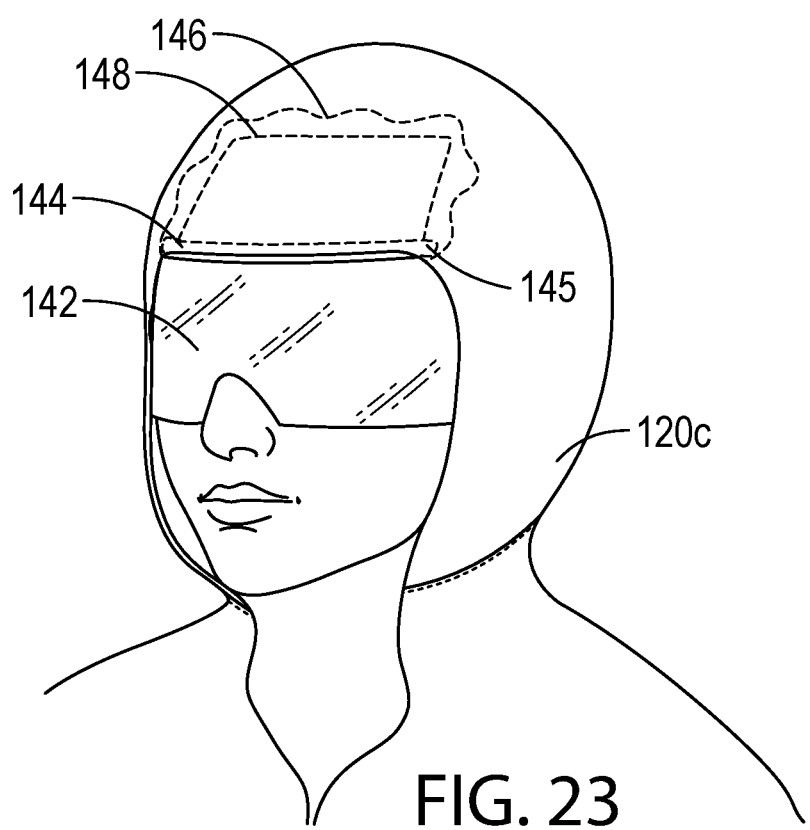
FIG. 23 illustrates yet another embodiment of the invention where a lens is stored in the forehead region of a hood.

FIG. 23 shows an embodiment similar to FIG. 6, but in this drawing hood 120c houses mixed reality lens 142 that is held in place in pocket 148 by tabs 145 and 144. When not in use lens 142 is slid upward and stored in the region or pocket 148. Line 146 depicts an area of hood 120c that may consist of a non-permeable layer as well as a layer that can be used to block EMF rays.

Figure 24:
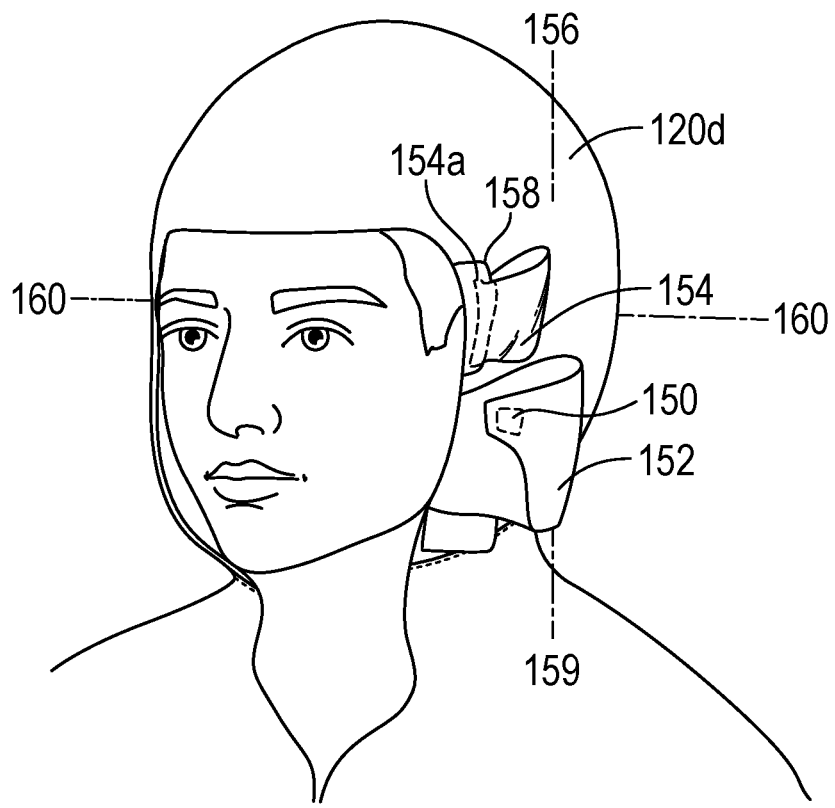
FIG. 24 illustrates an embodiment where a medical face shield and mask are stored in a region to the side of the headwear.
Figure 25:
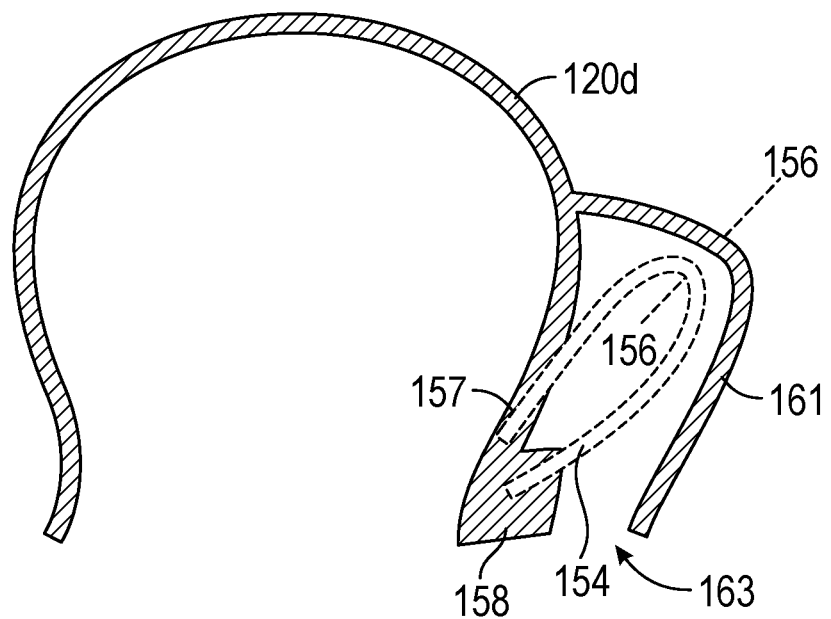
FIG. 25 illustrates a top view and cross section of FIG. 24

FIG. 24 shows the embodiment of the invention when mask 152 and eye shield 154 are exposed, but stored in the storable region at the side of headwear 120d. This arrangement is relevant as to when the headwear is used as a means for protection within the work safety or medical safety field. In use, the wearer would put on headwear 120d, remove tab 154a of eye shield 154 from pocket 158, and stretch it across his face and attach it to the other side of headwear 120d. He would then do the same with mask 152, attaching it by means of Velcro tab 150 to the other side of headwear 120d. Lens 154 is folded or creased along line 156 and mask 152 is folder or creased along lines 159. Lens 154, may also be a mixed reality lens which houses a camera and a projector. Lens 154 and mask 152 may be exposed, as is shown, or fully covered in a pocket as is shown in FIG. 25, where a top view of cross section 160 is scene. Here lens 154 is creased along lines 156 and tucked into pocket 158, where it is stored in pocket 163 at the side of headwear 120f by means of pocket 161.

In FIG. 25 lens 154 is attached to headwear 120d at contact point 157, but also held in the storable pocket or region by tab 158. Although not shown, mask 152 would be stored in a similar manner, when positioned to the side of headwear 120d.

Figure 26:
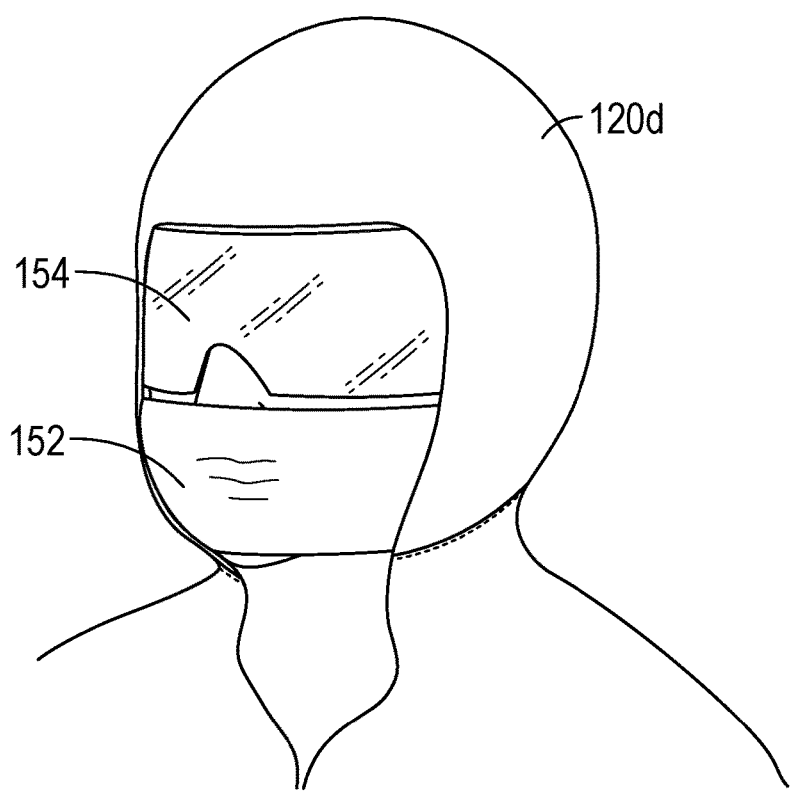
FIG. 26 illustrates the medical mask of FIG. 24 in use.

FIG. 26 shows headwear 120d, when mask 152 and eye shield 154 are extended across the user's face and are seperably attached to the other side of headwear 120d, and can now be used to protect one's face—eyes, nose, and mouth—during a medical emergency or procedure.

Figure 27:
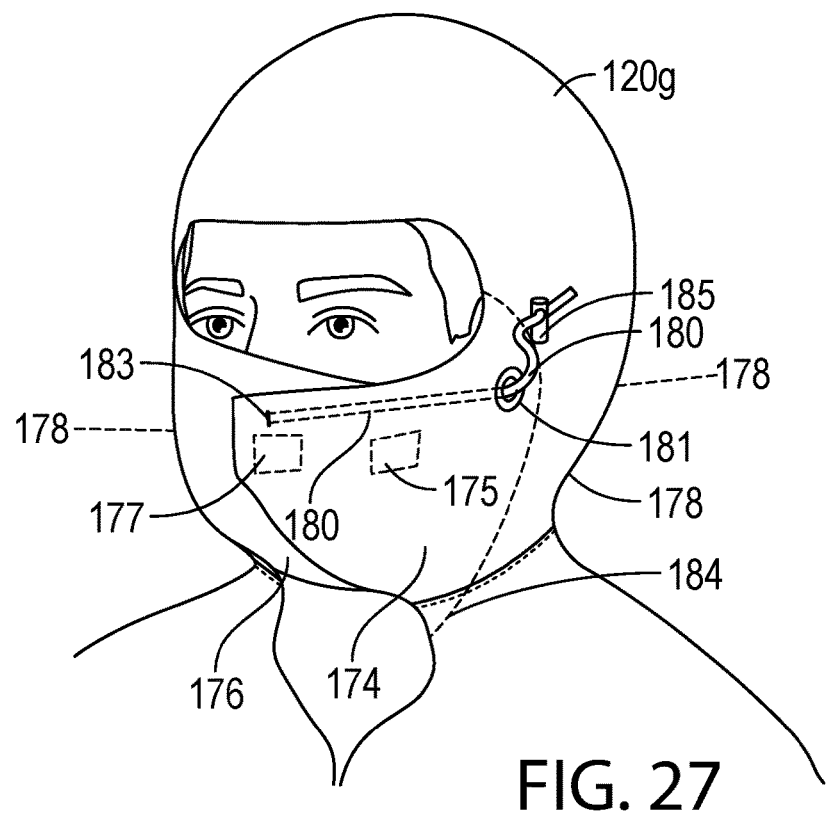
FIG. 27 illustrates a mask covering the user's face.

FIG. 27 shows an embodiment where mask 174 and mask 176 extend from alternate sides of hood 120g and meet in front of the users face, being attached by Velcro tabs 175 and 177. Retention string 180 begins at point 183 within the layers of mask 174, and extends to the middle of hood 120g, where it exits through grommet 181 and passes through cord lock 185. In order to help facilitate storing mask 174 within hood 120g, the user may pull retention string 180, which would compress mask 174 into a folded bundle. He would then, with his hands manually tuck or fold the folded bundle of mask 174 into the storable region by means of line or outer edge 184 of hood 120g.

When mask 174 is stretched across the users face, he may also pull retention string 180 further through cord lock 180 and grommet 181 to allow for a more snug fit. Retention string 180 may also exit hood 120g by grommet 181, then pass through cord lock 185, loop around and pass back through cord lock 181, then re-enter hood 120g through grommet 181 and re-attach at point 186 within hood 120g as is seen in FIG. 28.

Figure 28:
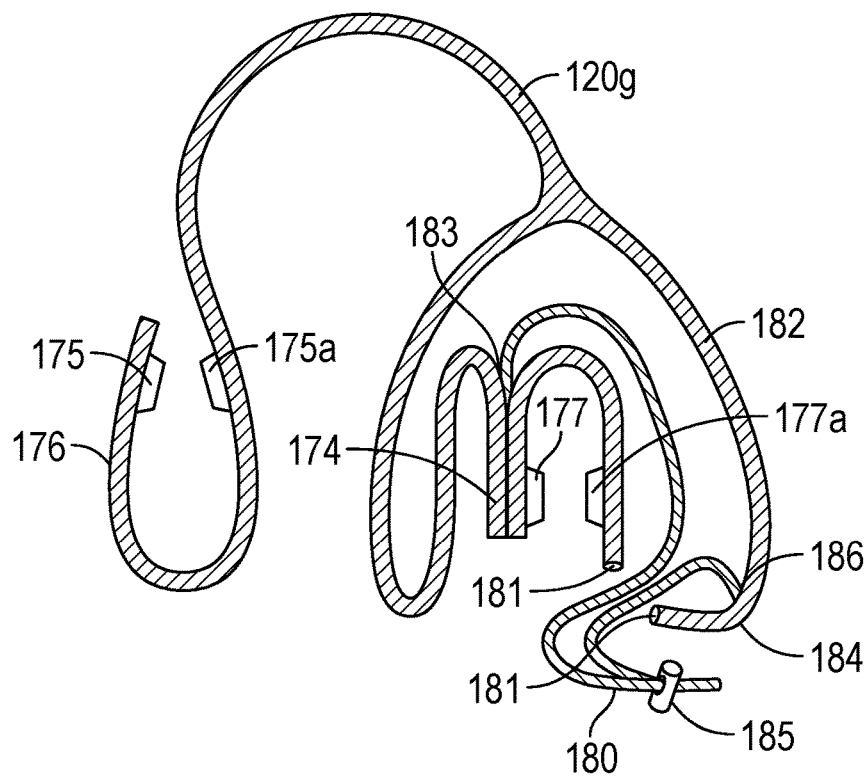
FIG. 28 shows a cross section and top view of FIG. 27, when the mask is stored.

When mask 176 and 174 are not used they are stored to the sides of headwear 120g, as is also seen in FIG. 28, where cross section 178 is further detailed. Here mask 176 is stored in the region, where it is attached to headwear 120g by means of Velcro tabs 175 and 175a. At the alternate side of headwear 120g, mask 174 is folded into itself, where Velcro tabs 177 and tabs 177a attach, creating an outer layer or pocket 182 as well as a self-storable pocket 189.

Figure 29:
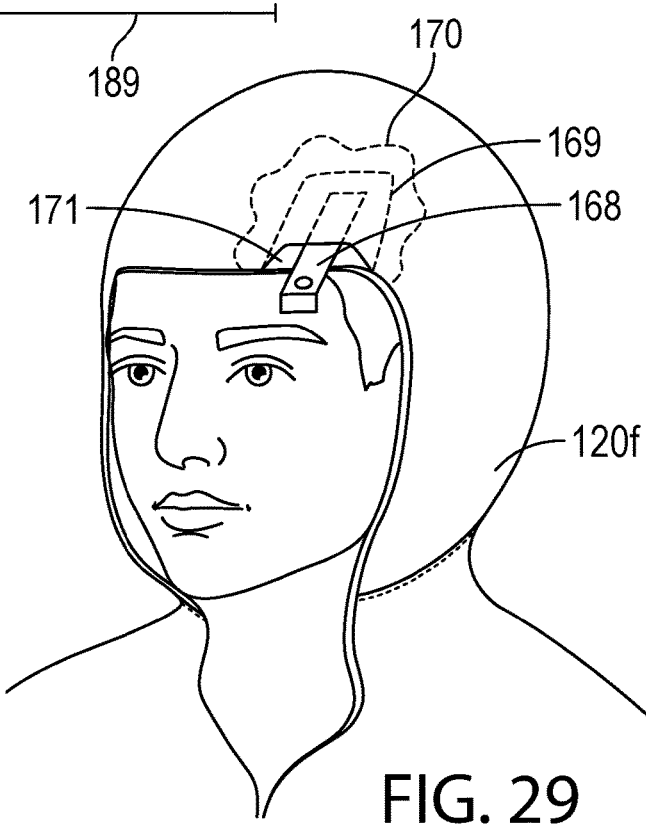
FIG. 29 shows an optical head mounted visual display stored in the forehead region of the user's head.

FIG. 29 shows hood 120f, housing a Google Glass 168, which exits pocket 169 through pocket opening 171. Google Glass 168 may slide in and out of pocket 169 when it's use is desired. To protect the user from EMF rays, material 170 may exist as an EMF blocker.

Figure 30:
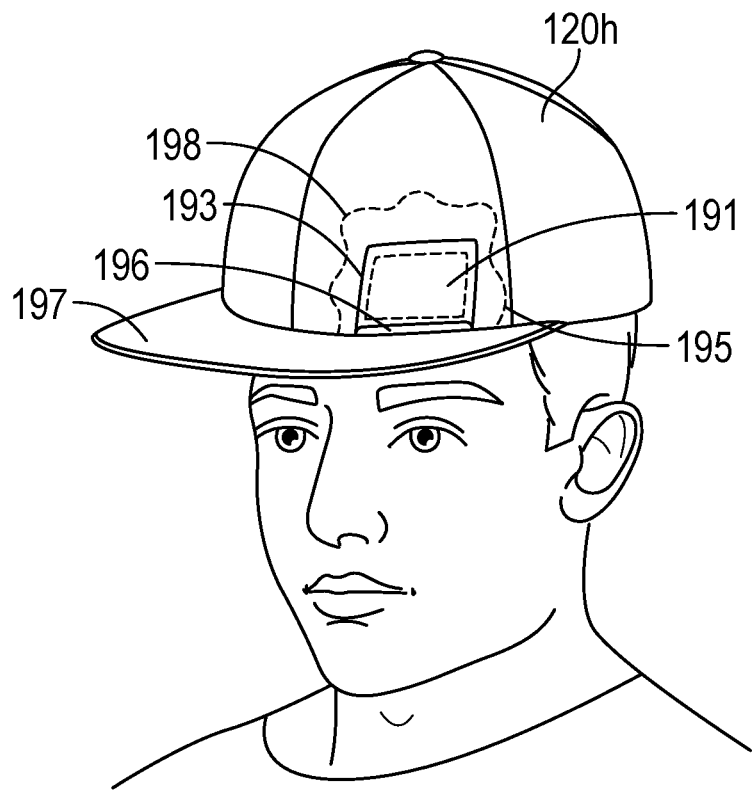
FIG. 30 illustrates a mixed reality lens built into a ball cap.

FIG. 30 shows a storable pocket 193 situated on ball cap 120h. Here, a mixed reality lens 191 is stored in front of a non-permeable layer 198, which protects the lens from fogging from the heat of the users head. Layer 198, may also be constructed of an EMF blocking material. In use the wearer slides lens 191 out of pocket 193 through slit or opening 196, where it would then cover the users eye, engaging him in a mixed reality media experience. Lens 191 may exist as a single unit for one eye, or it may stretch horizontally across the forehead region, where it would then cover both eyes, when positioned over the user's face. Using a mixed reality lens here would allow a fan at a baseball game to view up close an instant replay of a past action of a game he is watching or to view the score of that game as it fully engages him in the action as wall as any other interactive medium.

Figure 31:
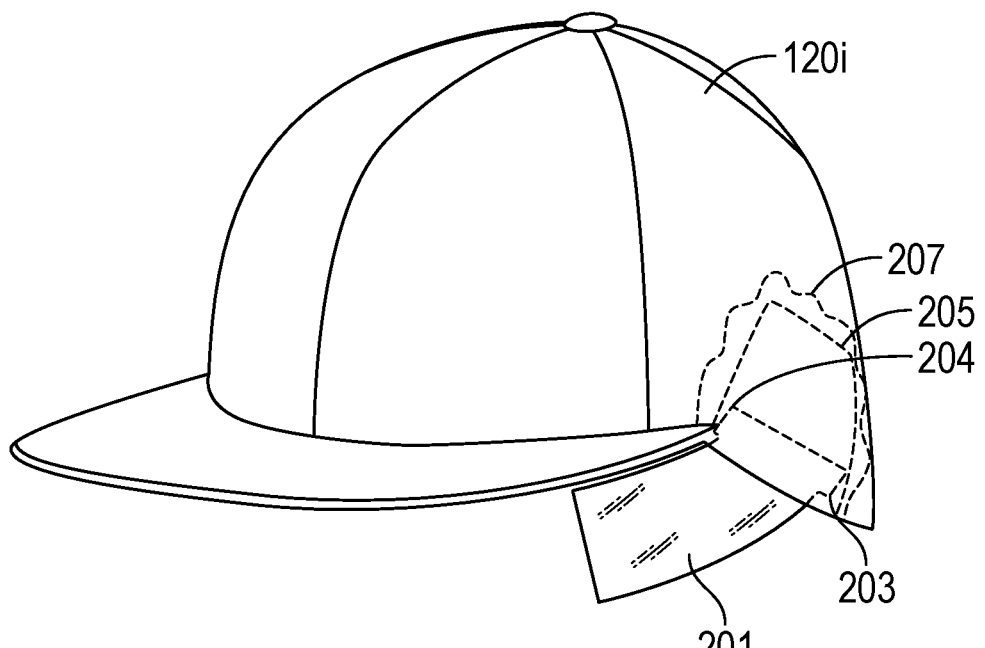
FIG. 31 illustrates another version of a mixed reality lens built into a ball cap.

FIG. 31 shows a similar version of ball cap 120h in FIG. 30, but here ball cap 120i houses a mixed reality lens 201, which is held into pocket 205 by means of tabs 203 and 204. Lens 201 may slide in and out of pocket 205 and is protected from fogging by non-permeable layer 207 which may also be constructed of an EMF blocker. Lens 201 may also be a mixed reality lens that can be used in the same manner as lens 191, as is previously described.

Figure 32:
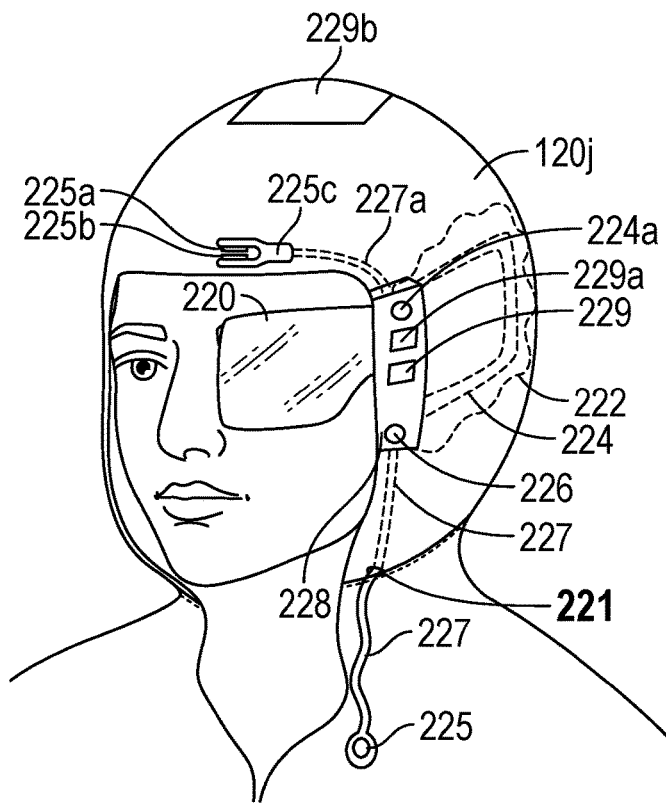
FIG. 32 illustrates yet another version of a mixed reality lens stored in an item of headwear.

FIG. 32 shows a similar drawing to the headwear in FIG. 1. But here lens 220 is attached to headwear 120j by means an electronic engine 228, which houses a camera 226 and a projector 224a. Electronic engine 228 has an opening built within its structure (not shown) where lens 220 is allowed to slide or pass through it, thus allowing lens 220 to be positioned over the wearer's eyes or stored in storable pocket or region 224. When lens 220 is stored to the side of the users head in pocket 224 it is protected from the body heat of the user by non-permeable layer 222, which may also be constructed of an EMF blocking material. Lens 220, when stored to the side of the user's head, may be stored within pocket 224, or left in the storable region fully exposed and uncovered. Electronic engine 228 may house a battery pack, multiple cameras and sensor, multiple projectors for a virtual reality or mixed reality experience, as well as solar powered receptor 229a or 229b, that would catch the ultraviolet rays from the sun, making the device a self powered unit.

The electronic engine here is the power behind the users mixed reality or virtual reality experience. The unit may also house a speaker 229. Connected internally to electronic engine 228 is cord 227, which exits headwear 120i at grommet 221 and extends to an end where touch sensor 225 is embedded into the material. Cord 227 may be constructed of a woven material or a metal wire connecting it to electronic engine 228. In use, when lens 220 is covering the user's face and the user is engaging in a virtual reality or mixed reality experience, it is typical that a mouse or mouse arrow is present. With the motion of his head he can direct the mouse to different windows or applications within his periphery. In order to select an application or window, he must be able to click on his choice. With his free hand he now has the ability to choose his window by touching sensor 225, which can emit a wireless Bluetooth signal to engine 228. Or sensor 225 may connect to electronic engine or electronic processor 228 by cord 227

It is also possible that string 227 is a woven string or the like, which is connected to electronic engine 228, and when the user pulls the string 227, it triggers a reaction within the engine or processor that causes the mouse to choose an application or window within his periphery.

Also positioned on headwear 120i is housing 225c which houses a magnetic sensors, a motion sensor or electronic sensors 225a and 225b which. When they touch one another a signal is sent to electronic engine 228 via electronic cord 227a. When Cord 227a is not present, sensors 225a and 225b are connected to electronic engine 228 via a Bluetooth connection. Housing 225c is constructed of a semi rigid plastic or rubber, making it flexible and bendable so it's appendages, which house sensors 225a and 225b, may touch one another. The user may also allow these sensors to touch one another by squeezing them together with his fingers, or by moving his head his head, or snapping his head forward or backward. In use when the user's mouse or arrow is on a preferred application or window, the user nods his head, causing 225a and 225b to connect, which then tells electronic engine 228 to register his choice, choosing a particular option. This allows the user to navigate his virtual reality world in a hands free manner.

A camera, a video camera, or a multitude of small cameras may also be attached to the end of retention string or cord 227 so that the user would pull the string away from his face and take pictures of his surroundings or himself.

Figure 33:
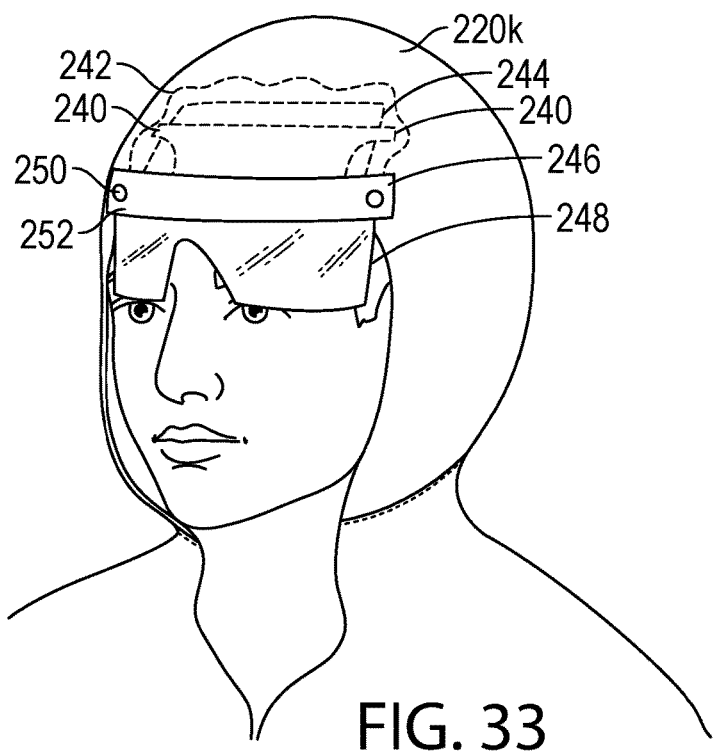
FIG. 33 illustrates a mixed reality lens stored in the forehead region of an item of headwear.

FIG. 33 shows a similar embodiment to FIG. 32, but here in headwear 220k, lens 248 passes through electronic engine 246, where it can be moved up and down. When not in use lens 248 is stored in region or pocket 244. Behind pocket 244 is non-permeable layer 242 which may also be a material that block EMF rays from the user. In use the wearer slides lens 248 down over his face, where the extended tabs 240 of lens 248 prevent the lens from falling out of pocket 244. Camera or projector 250 is situated on electronic engine 246. Although not shown, a mechanism such as a sensor string 227, 227a, and 225 as is show in FIG. 32, may be integrated into electronic engine 246.

Figure 34:
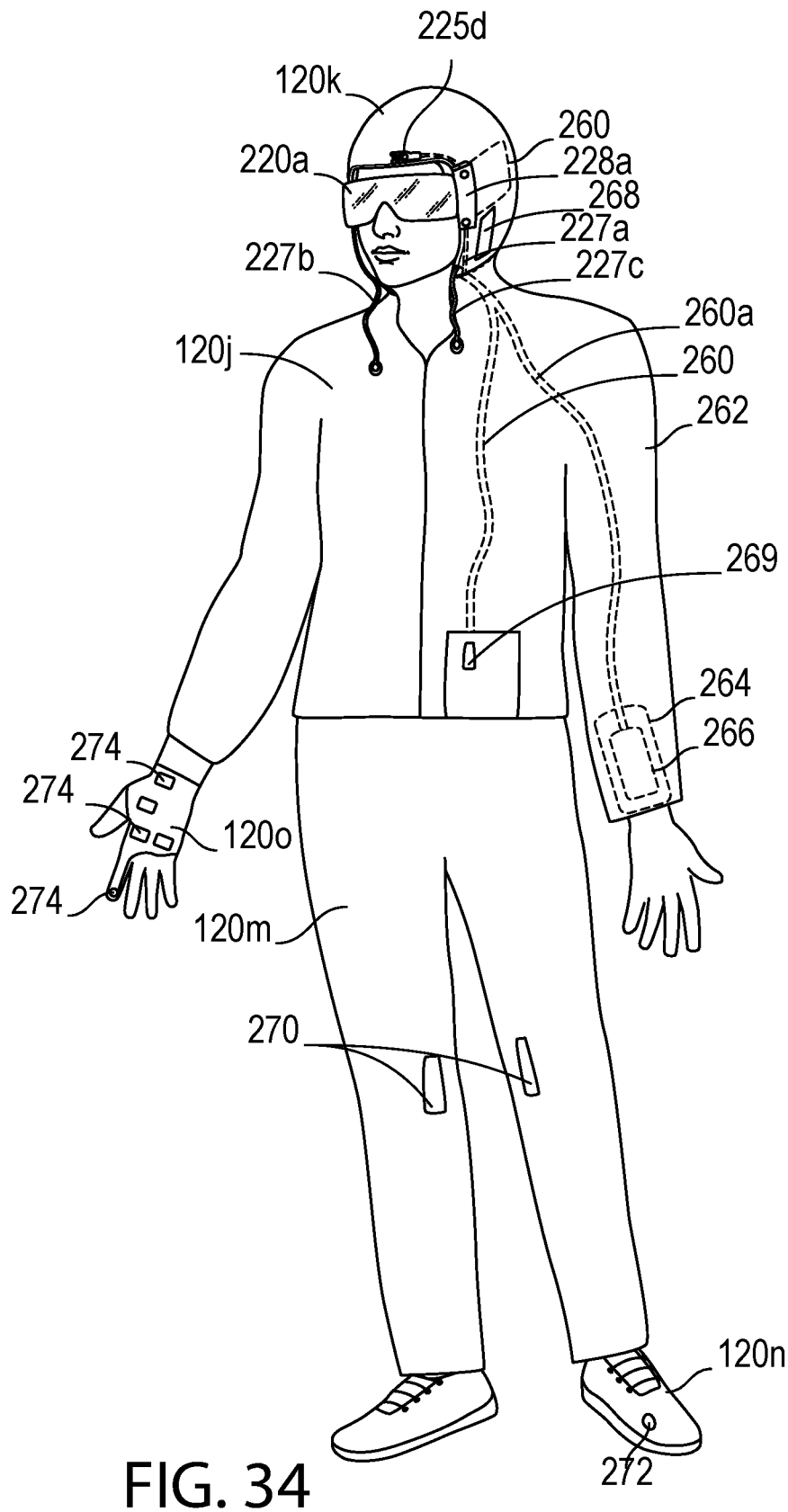
FIG. 34 illustrates a person wearing shoes, pants and a hooded sweatshirt with built in motion sensors.

FIG. 34 shows a similar embodiment to the headwear in FIG. 32, but here the headwear 120k is a hood of hooded sweatshirt 120j. Hood 120k houses lens 220a, which passes through electronic engine 228a and is stored in pocket or region 260. Motion sensor 225d is connected to electronic engine 228a. Embed throughout hooded sweat shirt 120k are motion sensor 269, 268 and 274 situated on sleeve extension 120o. Motion sensors 270 are situated in the knee area of pants 120m and motion sensor 272 is embedded into the sole of shoe 120n. The motion sensor may be connected wirelessly or through Bluetooth technology to electronic engine 228a or a cord 260, which connects engine 228a to sensor 269 as is shown.

In use, the wearer has lens 220a over his face and he is engaging in a mixed reality experience though a program or application. He may have an arrow or mouse like feature in his view. He may have a variety of screens present or applications or choices to choose from. He moves his head up and down, left to right to navigate the mouse to his different options. When he finds an option that fits his needs, he may do one of many things to select that option. He may tap his shoe, engaging sensor 272. Sensor 272 may also be positioned within the heel area.

He may put his left hand in his pocket and touch sensor 269. He may reach up to his hood and touch sensor 268. He may nod his head forward engaging sensor 225d, or he may take his left hand and touch any of sensors 274 on his right hand, or he may take his right hand and bend his fingers towards his sleeve or palm to engage any of sensor 274. He may also tap his knees together triggering sensors 270. Another option would be for him to take sensor wand 226 and slide it out of pocket 264 from sleeve 262, so it rests in the palm of his hand, where he can now grip it with his hand and fingers and wave it in multiple directions, which in turn will move the mouse in his program, and when he finds his selection, he can press a button on wand 266 to make his choice. Sensor wand 266 may be stored in pocket 264 when not in use and it may be connected wirelessly through Bluetooth to electronic engine 228a or via an electronic cord 260a. It is also to be noted that retention strings 227c and 227b, as well as acting as sensor for electronic engine or processor 228a, they may also act as strings or cords that would be used to tighten the fit of hood 120k around the user's head. The ends of retention strings 227c and 227b may also house a camera, a video camera, or a multitude of cameras and video cameras that would allow the user to take pictures or video and to then integrate that data into a mixed or virtual reality experience.

It is also possible that stings 227c and 227b—now having a camera or video camera attached—may be retractable into the hood with a pull and reel mechanism situated anywhere on the hood. In use the wearer would pull the string 227c or 227b away from the hoodie, locking its desired length in place. He would then take a picture or video, and pull it further away from his body, causing the pull and reel mechanism to retract the cord or string back into the body of the hoodie.

It is still, further to be noted that motion sensors 274 may be engaged to control the mouse or arrow in the users view, when the sleeve is moved in different directions, thus allowing the users fingers, hands, or arm to control the mouse within his view, in his mixed reality or virtual reality experience. Rather than having a mixed reality lens built into headwear 120k, it is also possible that a smart phone may be built in, and connected to the apparel, just as the electronic engine 228a is—via cords and sensor throughout.

Figure 35:
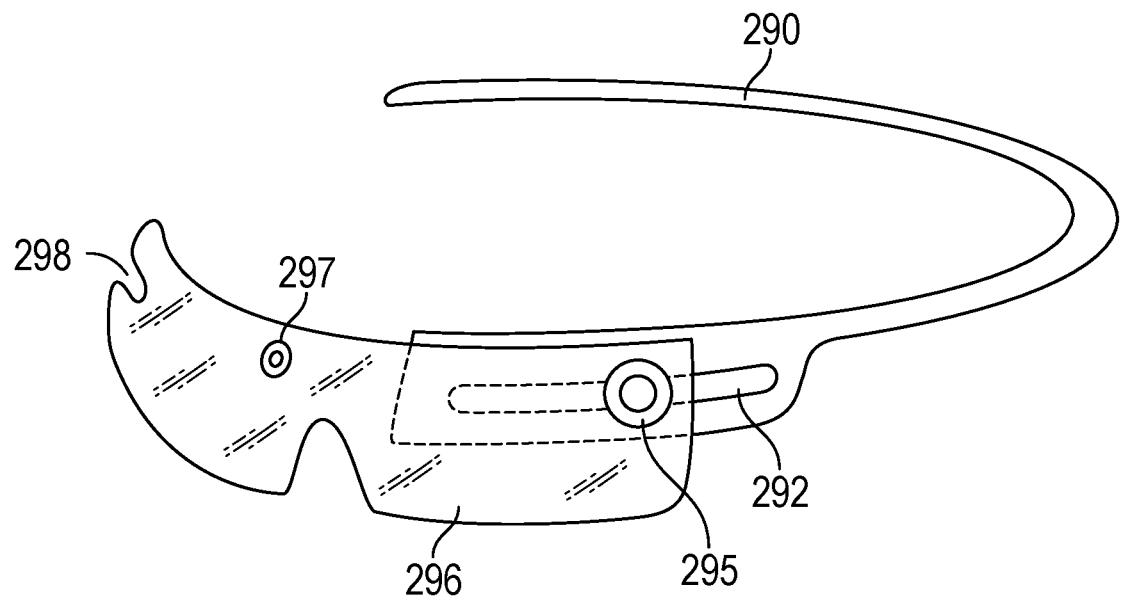
FIG. 35 illustrates a headset which has a mixed reality lens connected to it.

FIG. 35 shows another embodiment where mixed or augmented reality lens 296 is connected to frame 290 by locking means 295, which passes through horizontal track 292. Camera or projector 297 is embedded within lens 296. In use the wearer takes lens 296, slides it over his face and connects to the other side of frame 290 and engages in a mixed reality experience.

Figure 36:
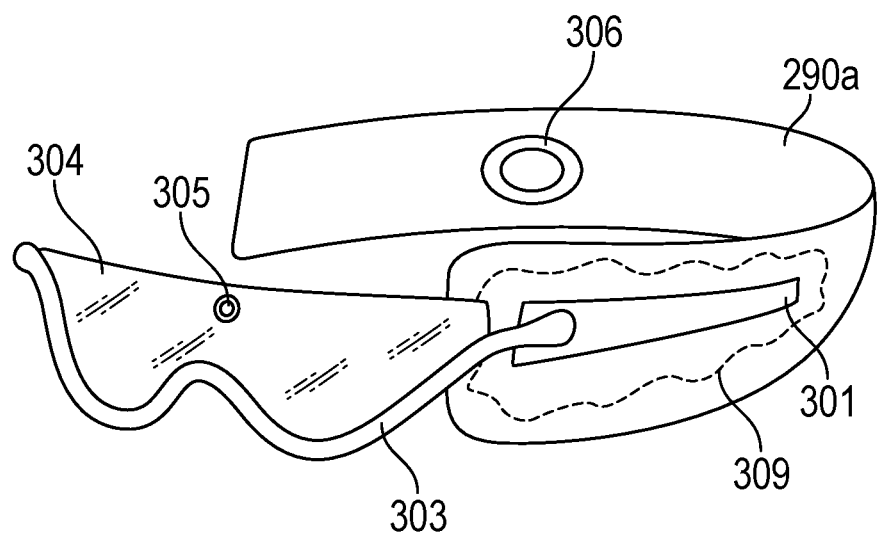
FIG. 36 illustrates another embodiment of FIG. 35.

FIG. 36 shows a similar embodiment to FIG. 35, but here lens 304 is connected to headwear or headband 290a by means of frame 303 which is attached to track 301 allowing the horizontal movement of lens 304 to either rest to the side of the user's head or to be positioned over the users face, where camera or projector 305 would facilitate a virtual reality or mixed reality experience. The electronic engine that fuels the mixed reality or virtual reality experience may exist within the frame 303 or within headband 290a, or both, simultaneously. When lens 304 is stored to the side of the users head, non-permeable layer 309 will may prevent moisture from the wearer's head from reaching the inside of the lens, which can fog the lens. This layer may also be constructed of an EMF blocker to prevent EMF rays from reaching the user's head. Embedded in headwear 290a is wireless speaker 306.

Figure 37A:
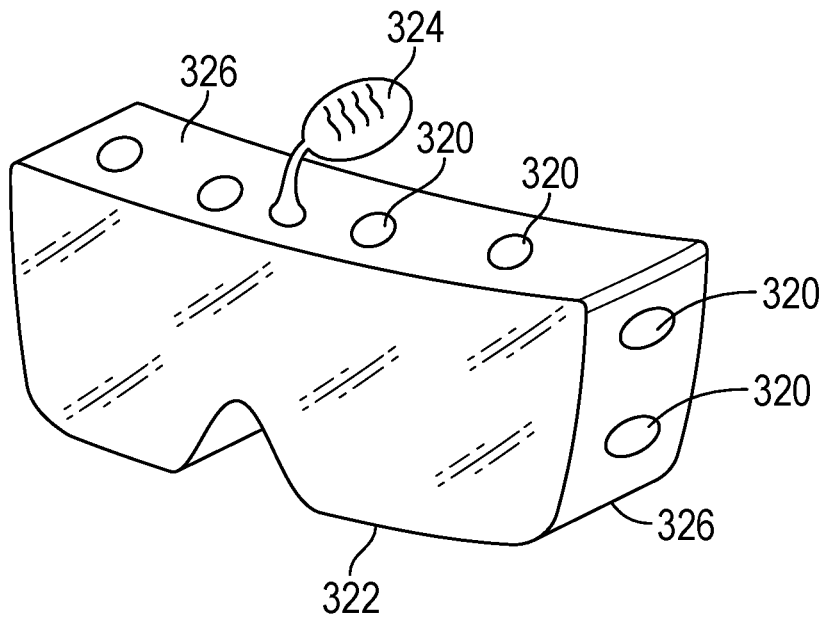
FIG. 37a illustrates a lens with built a built in ventilation mechanism.
Figure 37B:
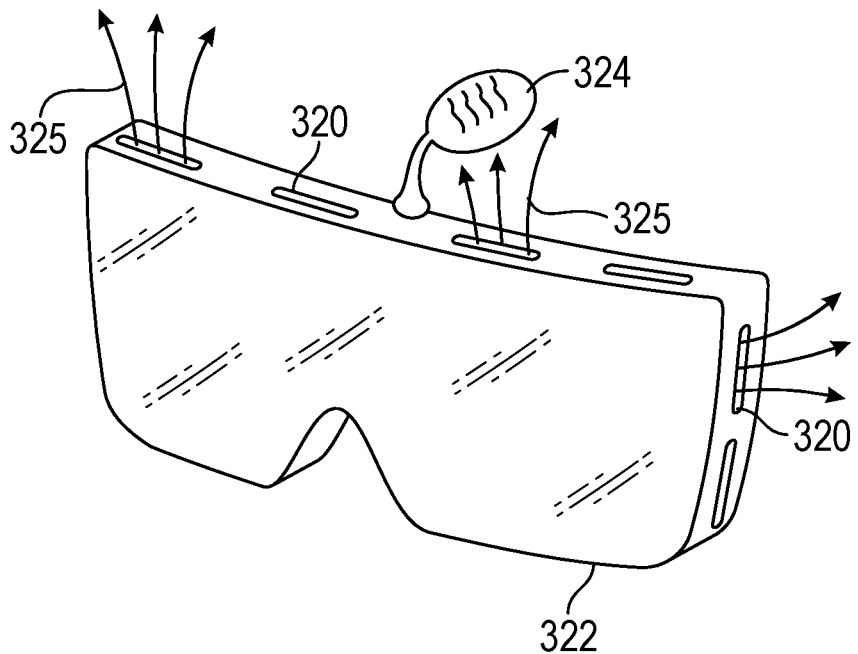
FIG. 37b illustrates another implementation of the lens with built a built in ventilation mechanism.

FIG. 37a shows lens 322 that is surrounded by a foam or rubber like frame 326 which has openings 320 embedded throughout. To prevent the fogging of the lens, the user would squeeze or pump the lens against his face—or to the side of his head when it is positioned there—and this would allow the air within the lens to be expelled as is seen in FIG. 37b, thus, preventing the lens from fogging. The user may also squeeze air pump 324 which would pump fresh air into the lens area, which would push out the heated air or moisture 325 from holes 320. Both solutions may be used together as a means for preventing the fogging of the interior of lens 322, and both mechanism may be used when a mixed reality or virtual reality lens is attached to an item of headwear as is shown in multiple embodiments in this application.

Figure 38:
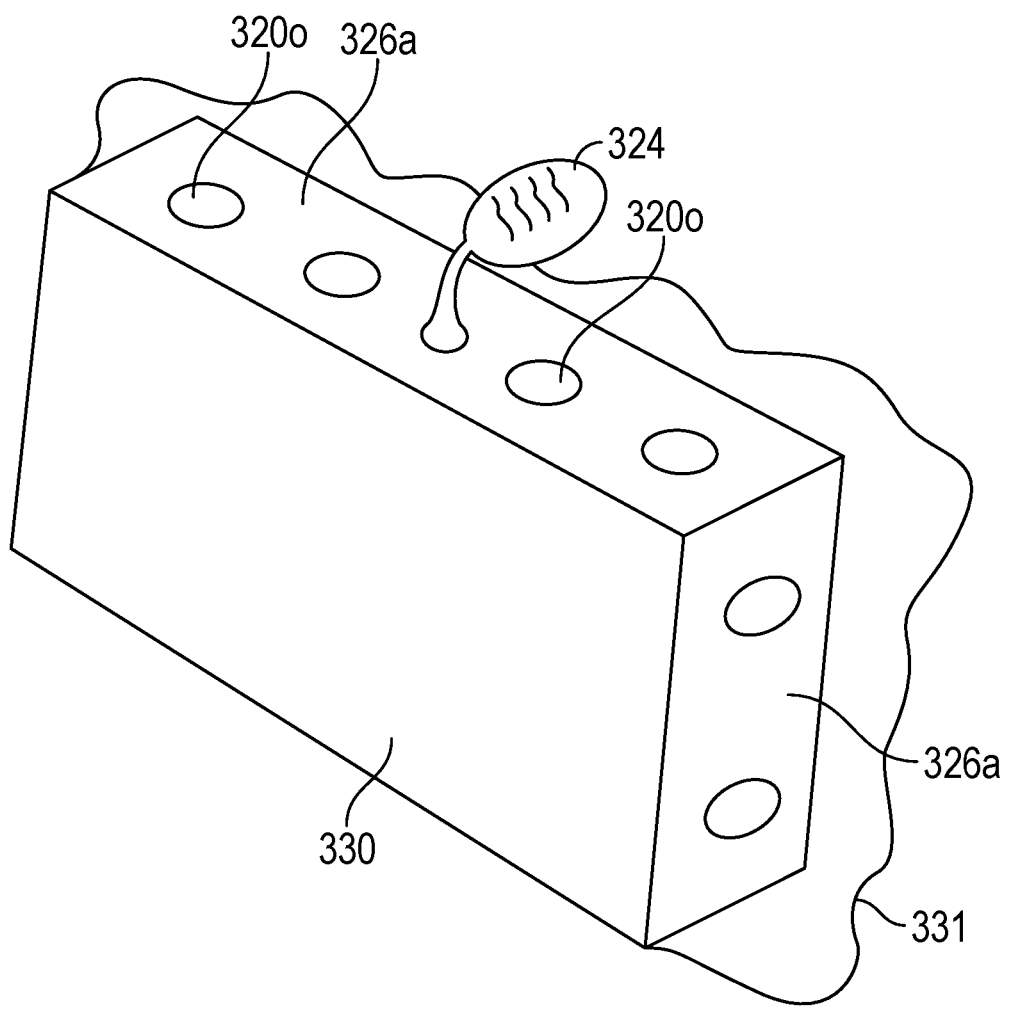
FIG. 38 illustrates a non-permeable layer of an item of headwear.

FIG. 38 shows an alternate embodiment to the non-permeable layer or EMF blocker that is positioned adjacent to the lens when stored to the side of one's head, or in the forehead region—as is explained throughout this application. Here non-permeable layer 330 is attached to foam or neoprene layer 326a which houses ventilation holes 320a as well as air pump 324—similar to FIG. 38. The lens (not present) would lye adjacent to layer 330. Line 331 depicts the fabric of the headwear of which the contraption is attached to.

In use, when the wearer begins to perspire, the moisture and hot air will build up within layer non-permeable layer 330 and fabric layer 331. To expel this moisture and hot air, the user would squeeze or pump the layer 330 against his head—similar to FIG. 38—and the air would be expelled through the air holes as is seen in FIG. 38. He may also expel the hot or humid air by squeezing air pump 324, which would deliver fresh air within the cavity. This would all for a comfortable wearing experience, as hot air and humid air will not build up within the cavity, as it is expelled.

It is also possible that the foam layer 326a is built in a manner that when pumped or pressed to the wearer's face, the top portion may be allowed to suck fresh outside air in, and the bottom portion would be allowed to pump the humid or hot air out—or vice versa. This embodiment would also work well for ski goggles.

Figure 39:
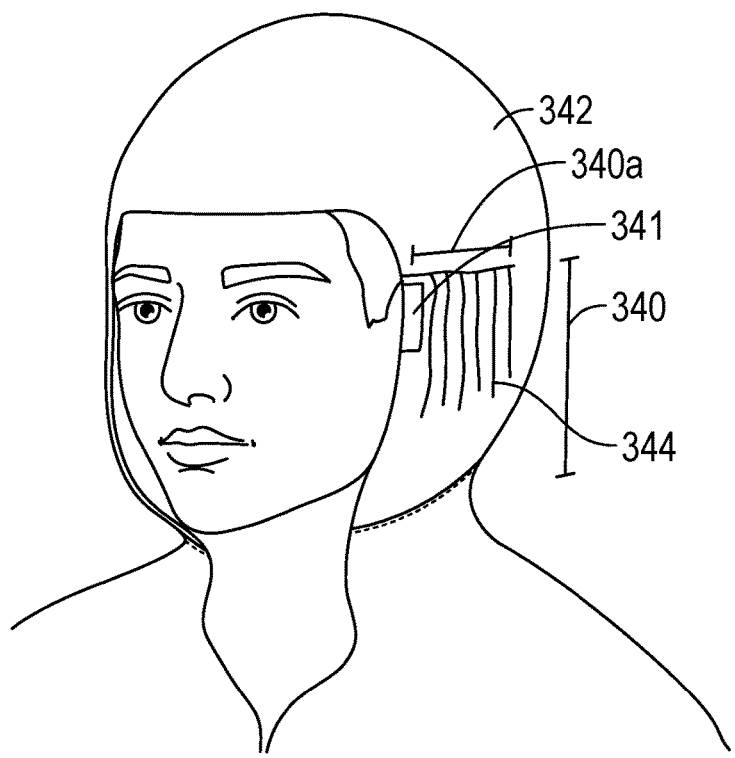
FIG. 39 illustrates another embodiment of a mask built into a hood.
Figure 40:
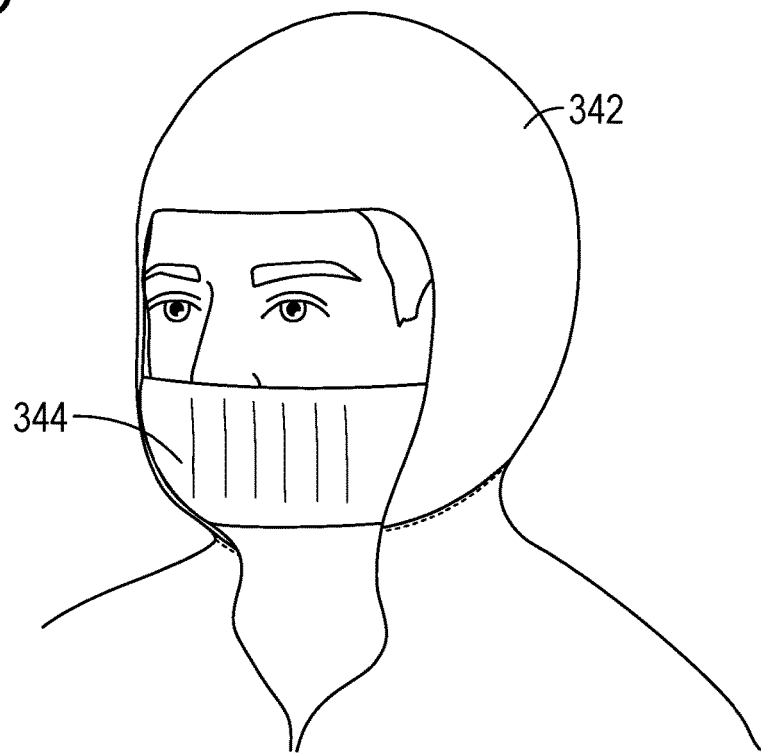
FIG. 40 illustrates the mask of FIG. 39 in use.

FIG. 39 shows a hood 342 of a hooded sweatshirt, where vertical area 340 and horizontal area 340a depict and area on the side of the hood, which is constructed of a very flexible and stretchable material 344. Material 344 may be constructed of rayon or a synthetic fiber, allows take up more surface area when stretched. Due to its flexible nature, it can contort into many shapes and sizes, yet when it is released from those forms, it quick snaps back or returns to its original shape and size. The remainder of hood 342 may also be flexible or rigid in nature. When the remainder of hood 342 is rigid and area 344 is flexible, the user may grab Velcro tab 341, stretch it out and across his face and attach it to an attaching means on the other side of his head, as is seen in FIG. 40. It is also possible that the entire hood may be constructed of the flexible material in area 340. When the mask is no longer needed, he undoes the Velcro tab, lets go of the mask, allowing area 344 to snap back into it's original position to the side of the user's head.

It will be understood that although the present invention has been hereinabove described with respect to several embodiments thereof, modifications may be made therein and thereto without necessarily departing from the spirit and scope of the invention as defined in the appended claims.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claim.

What is claimed is:

1. A headwear assembly, comprising:
at least one storage region secured to a portion of the headwear assembly, the at least one storage region including a first opening at a first end of the at least one storage region, the portion of the headwear assembly including a first side and a second side, the at least one storage region being secured to the first side;

at least one accessory including a first end and a second end, the first end of the at least one accessory is configured to be removable from the at least one storage region through the first opening of the at least one storage region, and movable from the first side to the second side for securing to the second side; and a retainer attached to the second end of the at least one accessory and configured to prevent removal of the second end of the at least one accessory from the at least one storage region;

wherein the retainer includes a retention element having a first end attached to the second end of the at least one accessory;

wherein the at least one storage region includes a second opening configured to allow passage of the retention element.

2. The headwear assembly according to claim 1, the retainer includes a retention element, wherein the second end of the at least one accessory is prevented from being removed from the storage region through the first opening.

3. The headwear assembly according to claim 1, wherein the retainer includes a locking mechanism, wherein a position of the locking mechanism is configured to be adjustable relative to the at least one storage region, thereby allowing selective adjustment of a position of the at least one accessory relative to the head of a user of the headwear assembly.

4. The headwear assembly according to claim 1, further comprising a retracting mechanism configured to return the at least one accessory to the at least one storage region from being removed from the at least one storage region.

5. The headwear assembly according to claim 1, further comprising a non-permeable layer configured to be positioned adjacent the at least one storage region and to prevent a passage of moisture to the at least one accessory when the at least one accessory is stored in the at least one storage region.

6. The headwear assembly according to claim 1, wherein the first end of the at least one accessory is configured to be secured to the second side subsequent to the removal of the first end of the at least one accessory from the at least one storage region.

7. The headwear assembly according to claim 6, wherein the first end of the at least one accessory is configured to be removably secured to the second side using a detachable element, wherein the detachable element includes at least one of the following: a cooperating male hook, a cooperating female loop, a fabric tab, a button, a slit, a hook-and-loop mechanism, a latch, a closure mechanism, a button snap, a snap grommet, a magnet, a magnet with at least one connecting tab, and any combination thereof.

8. The headwear assembly according to claim 1, wherein the headwear assembly includes at least one of the following: an eyeglass, sunglasses, a mask, a helmet, a headband, a hood of a clothing article, a military helmet, a construction helmet, a motorcycle helmet, a snowboard helmet, a headset, a virtual reality headset, an augmented reality headset, a gaming headset, and any combination thereof.

9. The headwear assembly according to claim 1, wherein the at least one accessory includes at least one of the following: a mask, a bandanna, a scarf, a lens, a goggle, a goggle retractable by a reel mechanism, a goggle retractable by a string, an encasement configured to receive at least one external device, a smartphone holder, a camera configured to be retractably secured within the at least one storage region, a virtual reality device configured to be retractably secured within the at least one storage region, a camera holder, an augmented reality lens, an augmented reality device configured to be retractably secured within the at least one storage region, and any combination thereof.

10. The headwear assembly according to claim 1, wherein the at least one storage region is configured to be secured to the portion of the headwear assembly using at least one of the following: permanently secured to the portion of the headwear assembly, detachably secured to the portion of the headwear assembly, and any combination thereof.

11. A headwear assembly, comprising:

a headwear having a first side and a second side; and at least one accessory configured to be secured to the first side in a first position, the at least one accessory is configured to be movable from the first position to a second position, wherein, in the second position, a portion of the at least one accessory is configured to be secured to the second side of the headwear, thereby covering a portion of a head of the user of the headwear assembly, the at least one accessory including a first end and a second end, the first end of the at least one accessory is configured to be removable from at least one storage region, secured to a portion of the headwear assembly, through a first opening of the at least one storage region, and movable from the first side to the second side for securing to the second side; and a retainer attached to the second end of the at least one accessory and configured to prevent removal of the second end of the at least one accessory from the at least one storage region;

wherein the retainer includes a retention element having a first end attached to the second end of the at least one accessory;

wherein the at least one storage region includes a second opening configured to allow passage of the retention element.

12. The headwear assembly according to claim 11, wherein the headwear includes at least one track, the at least one accessory is configured to slide on the track.

13. The headwear assembly according to claim 11, wherein the headwear includes a frame including at least one track;

a locking mechanism coupled to the at least one track having a first end and a second end and configured to secure the at least one accessory in at least one of the first position and the second position;

wherein, in the first position, the locking mechanism is positioned at the first end of the at least one track, and in the second position, the locking mechanism is positioned at the second end of the at least one track.

14. The headwear assembly according to claim 11, wherein the at least one accessory is configured to be secured to the portion of the headwear assembly using at least one of the following: permanently secured to the portion of the headwear assembly, detachably secured to the portion of the headwear assembly, and any combination thereof.

15. The headwear assembly according to of claim 11, wherein the headwear assembly includes at least one of the following: an eyeglass, sunglasses, a mask, a helmet, a headband, a hat, a ball cap, a hood of a clothing article, a military helmet, a construction helmet, a motorcycle helmet, a snowboard helmet, a headset, a virtual reality headset, an augmented reality headset, and any combination thereof.

16. The headwear assembly according to claim 11, wherein the at least one accessory includes at least one of the following: a mask, a bug mask, a medical mask, a bandanna, a lens, a goggle, a goggle retractable by a reel mechanism, a goggle retractable by a string, an encasement configured to receive at least one external device, a smartphone holder, a camera, a virtual reality device, an augmented reality device, a camera holder, and any combination thereof.

\* \* \* \* \*